(12) United States Patent
Shia

(10) Patent No.: US 11,925,321 B2
(45) Date of Patent: Mar. 12, 2024

(54) ANTI-TWIST TIP FOR STEERABLE CATHETER

(71) Applicant: CANON U.S.A., INC., Melville, NY (US)

(72) Inventor: Benedict Shia, Needham, MA (US)

(73) Assignee: Canon U.S.A., Inc., Melville, NY (US)

(*) Notice: Subject to any disclaimer, the term of this patent is extended or adjusted under 35 U.S.C. 154(b) by 100 days.

(21) Appl. No.: 17/362,560

(22) Filed: Jun. 29, 2021

(65) Prior Publication Data

US 2022/0039635 A1 Feb. 10, 2022

Related U.S. Application Data

(60) Provisional application No. 63/152,189, filed on Feb. 22, 2021, provisional application No. 63/062,121, filed on Aug. 6, 2020.

(51) Int. Cl.
*A61B 1/00* (2006.01)
*A61B 1/005* (2006.01)
(Continued)

(52) U.S. Cl.
CPC ........ *A61B 1/0055* (2013.01); *A61B 1/00154* (2013.01); *A61B 1/0057* (2013.01);
(Continued)

(58) Field of Classification Search
CPC ....... A61B 1/0055; A61B 1/05; A61B 1/0056; A61B 1/0057; A61B 1/126; A61B 1/0011;
(Continued)

(56) References Cited

U.S. PATENT DOCUMENTS 8,692,874 B2 * 4/2014 Adler .................... G09B 23/30
600/160
8,864,652 B2 10/2014 Diolaiti et al.
(Continued)

FOREIGN PATENT DOCUMENTS

JP 2009-125389 A 6/2009
JP 2014-533996 A 12/2014
(Continued)

*Primary Examiner* — Anh Tuan T Nguyen
*Assistant Examiner* — Sung Ham
(74) *Attorney, Agent, or Firm* — Canon U.S.A., Inc. IP Division

(57) ABSTRACT

A steerable catheter driven by a robotic controller comprises: a catheter body having a tool channel extending from a proximal to a distal end; and a positioning mechanism configured to be coupled with an imaging device and to be slidably inserted into and/or withdrawn from the catheter body through the tool channel. The positioning mechanism and/or the catheter body include an anti-twist feature configured to interlock the catheter body to the imaging device at the distal end of the catheter body so as to prevent rotation of the imaging device within the tool channel. Anti-twist features include bumps or recesses formed in the tool channel inner surface to be interlocked with one or more features formed on the positioning mechanism outer surface. Position and/or orientation of the imaging device remain substantially unchanged with respect to the tool channel when the catheter body is steered by an actuating force.

26 Claims, 12 Drawing Sheets

(51) Int. Cl.
*A61B 1/015* (2006.01)
*A61B 1/018* (2006.01)
*A61B 1/05* (2006.01)
*A61M 25/00* (2006.01)
*A61M 25/01* (2006.01)

(52) U.S. Cl.
CPC .............. *A61B 1/015* (2013.01); *A61B 1/018* (2013.01); *A61B 1/05* (2013.01); *A61M 2025/0059* (2013.01); *A61M 2025/006* (2013.01); *A61M 25/0147* (2013.01)

(58) Field of Classification Search
CPC ..... A61B 1/00154; A61B 1/018; A61B 1/015; A61B 1/051; A61M 25/0147; A61M 2025/0059; A61M 2025/006
See application file for complete search history.

(56) References Cited

U.S. PATENT DOCUMENTS

| | | | |
|---|---|---|---|
| 9,539,726 B2 | 1/2017 | Simaan et al. | |
| 9,572,628 B2 | 2/2017 | Zubiate et al. | |
| 10,275,899 B2 | 4/2019 | Geissler et al. | |
| 10,376,134 B2 | 8/2019 | Schlesinger et al. | |
| 10,624,701 B2 | 4/2020 | Hunter et al. | |
| 2003/0028100 A1 | 2/2003 | Tearney et al. | |
| 2003/0163128 A1 | 8/2003 | Patil et al. | |
| 2005/0273090 A1 | 12/2005 | Nieman et al. | |
| 2006/0020165 A1* | 1/2006 | Adams | A61B 1/00142 600/157 |
| 2010/0210905 A1* | 8/2010 | Takeuchi | A61B 1/00135 600/110 |
| 2011/0026787 A1 | 2/2011 | Hale et al. | |
| 2013/0096572 A1* | 4/2013 | Donhowe | A61B 34/10 606/130 |
| 2013/0204126 A1 | 8/2013 | Namati et al. | |
| 2014/0371764 A1* | 12/2014 | Oyola | A61B 1/008 606/130 |
| 2016/0262840 A1 | 9/2016 | Zubiate et al. | |
| 2017/0135584 A1 | 5/2017 | Tearney et al. | |
| 2017/0296038 A1* | 10/2017 | Gordon | A61B 1/015 |
| 2017/0303824 A1 | 10/2017 | Schlesinger et al. | |
| 2021/0161387 A1 | 6/2021 | Wang et al. | |

FOREIGN PATENT DOCUMENTS

| | | |
|---|---|---|
| JP | 2015-034875 A | 2/2015 |
| JP | 2016-529033 A | 9/2016 |
| WO | 2014/046618 A1 | 3/2014 |
| WO | 2017/087579 A1 | 5/2017 |

\* cited by examiner

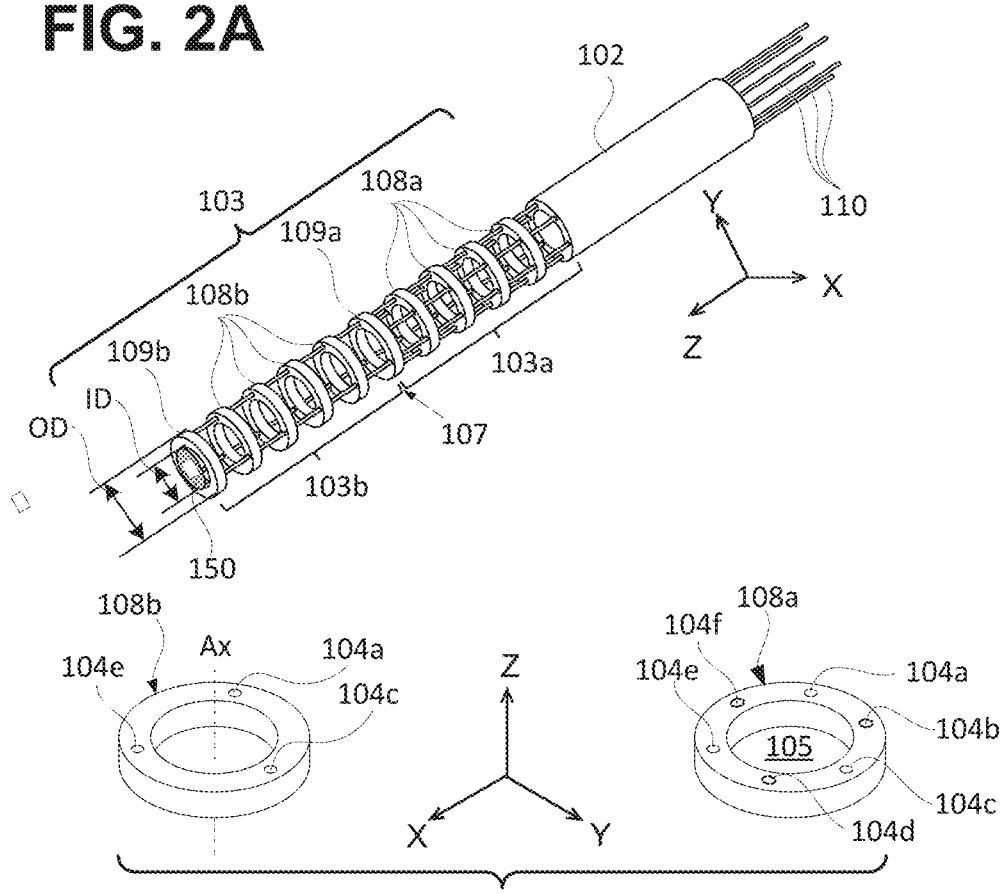
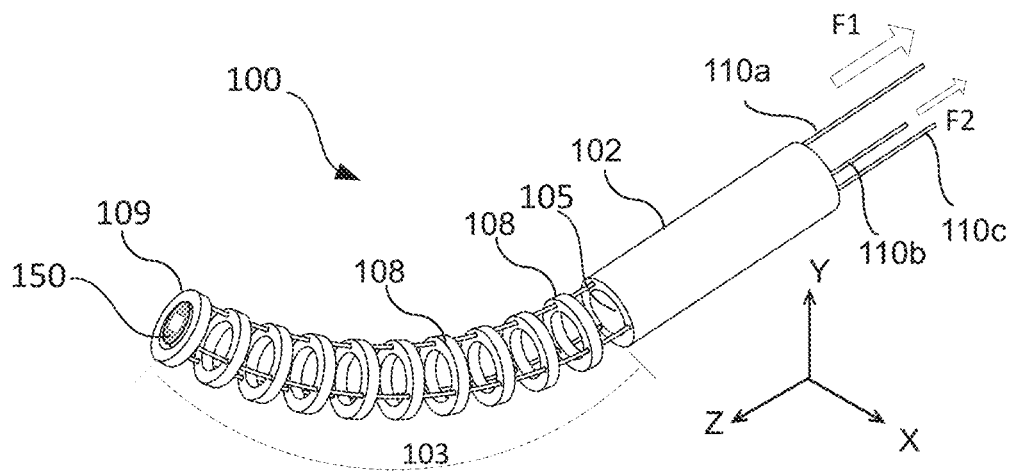

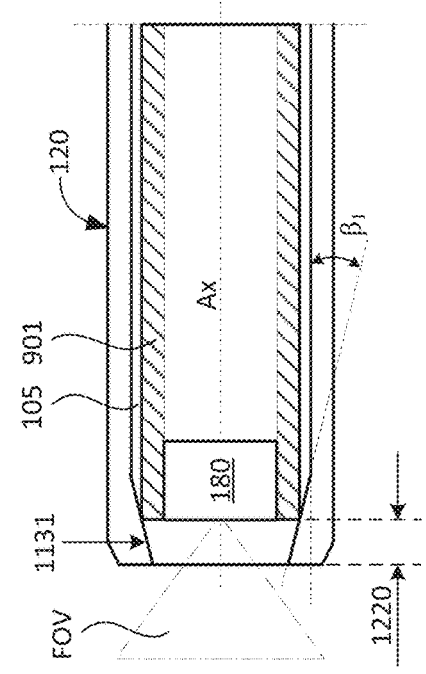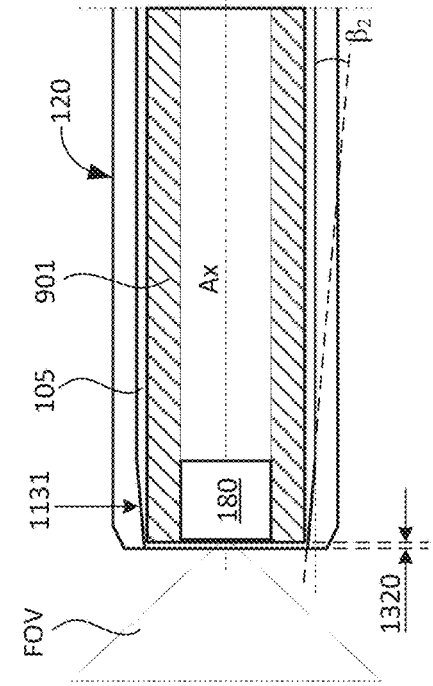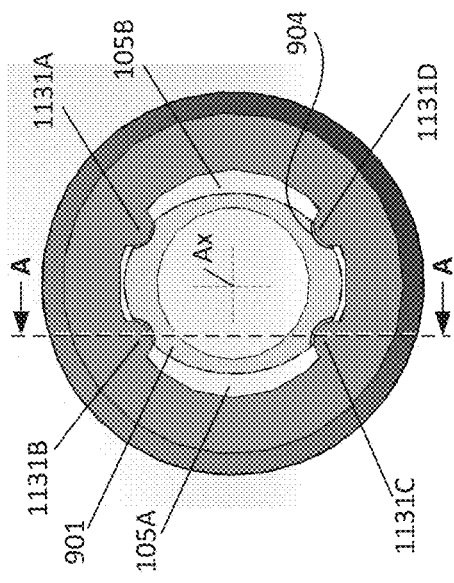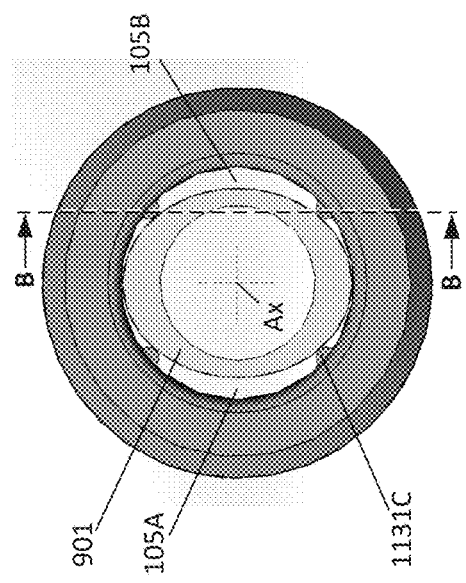

ANTI-TWIST TIP FOR STEERABLE CATHETER

CROSS-REFERENCE TO RELATED APPLICATIONS

The present application claims priority to U.S. provisional applications No. 63/062,121 filed Aug. 6, 2020, and U.S. provisional applications No. 63/152,189 filed Feb. 22, 2021, the disclosures of which are hereby incorporated by reference in their entirety for all purposes. Priority benefit is claimed under 35 U.S.C. § 119(e).

BACKGROUND INFORMATION

Field of Disclosure

The present disclosure relates to medical devices. More particularly, the disclosure is directed to various embodiments of an anti-twist tip for steerable medical devices such as catheters and endoscopes equipped with a removable imaging device such as a camera.

Description of Related Art

Steerable medical devices, e.g., catheters, endoscopes, etc., are remotely operated by applying an actuating force (pulling or pushing force) on metal wires to robotically articulate the distal section of the device. The actuation of the distal section can be advantageously improved with intra-operative image guidance provided by an imaging device, such as a camera or videoscope. A handheld controller (e.g. a gamepad controller) is used as an interface for interaction between the user and the robotic system to control endoscope navigation within the body of a patient. A display device, such as a liquid crystal display (LDC) monitor provided in a console or attached to a wall, displays an image of the camera's field of view (FOV image) to assist the user in navigating the endoscope through the patient's anatomy to reach a target location inside the patient.

As the user manipulates the endoscope or catheter inside the patient's anatomy, the camera transfers the camera's FOV image the display device to be displayed with its own upright axis displayed as the upright axis of the image on the display device. Ideally, this should allow the user to relate to the endoscopic image as if the user's own eyes were actually inside the endoscope cavity. This is known as a first-person-view (FPV) navigation. However, the distal tip of the steerable device can twist during navigation, resulting in errors in the correlation of steering inputs to visual guidance. Twisting of the distal tip of robotic catheter can occur due to numerous factors, as described in U.S. Pat. No. 9,572,628 which is incorporated by reference herein in its entirety. In the state of the art, there are numerous publications that propose techniques which can maintain the proper upright gravity-leveled orientation of the endoscopic image regardless of how the steerable device is being manipulated. Techniques for controlling rotation of the displayed image include measuring the orientation of the endoscope, and then rotating the endoscopic image optically, mechanically or electronically to compensate for the change in orientation of the endoscope tip or rotation of the camera. See fore example, patent application publications US 2011/0026787, US 2013/0204126, and U.S. Pat. No. 10,275,899.

In addition, U.S. patent Ser. No. 10/376,134 B2 describes a steerable device equipped with a fiber-based shape sensor that requires the orientation of the shape sensor to remain fixed relative to the tip of the device. This patent describes an anti-twist feature to ensure proper orientation of an imaging device. The camera used for visualization is permanently fixed in the distal portion of the device, so twisting is addressed in this manner. U.S. Pat. No. 8,864,652 B2 describes another steerable medical device that has an articulating camera inserted through a dedicated passage, and articulatable surgical tools respectively inserted through separate passages. In this patent, the camera is permanently attached to the distal end of the device, and the device tip also incorporates a sensor to determine positon and/or orientation so that the articulation of surgical instruments does not cause a collision with the camera.

A new type of steerable medical device is known as a Medical Continuum Robot (MCR) which operates differently from a conventional steerable medical device. Conventional endoscopes are designed with an integrated camera affixed to the distal end of the device, and one or more separate working channels are used during a procedure to allow access for instruments, and/or to allow suction and irrigation of fluids. Unlike conventional endoscopes, the robotic MCR device is designed to have a reduced number of channels (preferably a single channel) through which a flexible videoscope (camera) is inserted to provide image guidance during navigation, and the same channel is often used to allow access for instruments and/or to allow suction and irrigation of fluids. The use of a single channel for the imaging device and tools allows for a smaller overall profile than conventional endoscope devices where the camera is integrated into the device and separate channels are used to allow access for tools and fluids. An example of a continuum robot is described in U.S. Pat. No. 9,539,726. All of the above-referenced patents are incorporated by reference herein in their entirety.

In the MCR device, since the videoscope (camera) is not fixed to the steerable device, the suction and irrigation functions can be performed with the camera in place, by providing a certain clearance space between the camera and the inner diameter (ID) of the single channel. However, the MCR device has multiple bending sections, and each bending section is manipulated by a plurality of control wires that steer the MCR device through tortuous anatomies. Pulling and pushing on the control wires causes length changes (displacement) in the wires within the MCR. These changes cause the individual bending sections to deflect the steerable instrument with three or more degrees of freedom (DOF). The control wire or wires being pulled bend to form an inner bend radius, and the wire or wires that are pushed bend along an outer bend radius.

Due to the structure of the distal bending section, the MCR can twist due to the actuation inputs and due to friction with the anatomy through which the catheter navigates. Since the camera is not secured to the tip of the MCR device, the tip of the MCR is free to twist or rotate around the camera. Alternatively, the camera may rotate with respect to the catheter body when the tip of the MCR bends and/or moves. The twisting or rotation of the catheter tip around the camera results in a discrepancy between the view of the camera and the steering inputs provided at the proximal end of the catheter through the controller. Therefore, there is a need for an improved MCR system which can prevent negative effects of camera rotation, while maintaining appropriate correlation between the orientation of the camera view, the orientation of the gamepad controller, and the orientation of the catheter tip.

SUMMARY OF EXEMPLARY EMBODIMENTS

According to at least one embodiment disclosed herein, there is provided a steerable medical catheter to be driven by a medical continuum robot (MCR) system controller comprising: a catheter body and an anti-twist feature arranged in a distal section of the catheter body. The catheter body has a tool channel and a plurality of control wires arranged along the wall of the tool channel. The control wires transfer an actuating force from an actuator unit to the distal section so as to steer at least one portion of the catheter body. The anti-twist feature is configured to be coupled with an imaging device inserted through the tool channel. A distal tip of the catheter body is configured to be interlocked with the anti-twist feature such that a position and/or orientation of the imaging device remains substantially unchanged with respect to the distal tip when the at least one portion of the catheter body is steered by the actuating force. The catheter body is longitudinally flexible, and the anti-twist feature resists twisting of the catheter tip and/or prevents rotation of the imaging device during bending and navigation of the catheter.

In all embodiments, the MCR system includes a removable camera configured to be interlocked with the catheter body via a positioning mechanism. The positioning mechanism and/or the distal tip of the catheter body has an anti-twist feature that prevents rotation of the camera, reinforces the distal tip of the catheter body, and reduces twisting of the catheter distal tip. The anti-twist feature will keep the orientation of the camera and distal tip more consistent, and thus allow more intuitive navigation since the camera view will better correspond to navigation inputs, e.g., right will be right, and up will be up, etc., throughout the procedure. The anti-twist feature will also provide a gap between the camera and the catheter inner wall to allow suction and irrigation to be performed without having to remove the camera. The anti-twist feature may increase the profile of the camera, and reduce the size of the opening through the catheter tip. That increase/reduction is optimized in the various embodiments disclosed herein, so that the overall profile of the catheter body is minimized as much as possible. In this manner, during image guidance, the gap between the camera and the catheter inner wall can be efficiently used to supply/remove fluids (e.g., water or gas) to clean bodily substances (e.g., mucus) blocking the camera view. In some embodiments, the anti-twist feature includes keyways and keying tabs that removably engage when the camera is inserted into the catheter tool channel. In some embodiments, the anti-twist feature is built-in the catheter tip in the form of tapered ribs (male features). The features are largest in size at the distal end and taper down in the proximal direction.

These and other objectives, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Aspects of the present disclosure are best understood by reading the following detailed description in light of the accompanying figures. It is noted that, in accordance with the standard practice, the various features of the drawings are not drawn to scale and to not represent actual components. Several details such as dimensions of the various features may be arbitrarily increased or reduced for ease of illustration. In addition, reference numerals and/or letters are repeated in the various examples to depict similar components and/or functionality. This repetition is for the purpose of simplicity and clarity and does not in itself limit the various embodiments and/or configurations the same components discussed.

FIG. 2A, FIG. 2B, and FIG. 2C illustrate further details of the steerable instrument 100, according to an exemplary embodiment of the present disclosure.

FIG. 12A is a front view as seen from the distal end of the catheter 100, and FIG. 12B is a sectional view taken along section AA of the catheter body in the lengthwise direction. In FIG. 12A and FIG. 12B, the distal tip 120 of the catheter 100 is provided with a plurality of bumps 1131A, 1131B, 1131C, and 1131D formed in the tool channel thereof at a maximum material condition.

FIG. 13A is a front view as seen from the distal end of the catheter 100, and FIG. 13B is a sectional view taken along section BB of the catheter body in the lengthwise direction. In FIG. 13A and FIG. 13B, the distal tip 120 of the catheter 100 is provided with a plurality of bumps 1131A, 1131B, 1131C, and 1131D formed in the tool channel thereof at a minimum material condition.

DETAILED DESCRIPTION OF EXEMPLARY EMBODIMENTS

Figure 1:
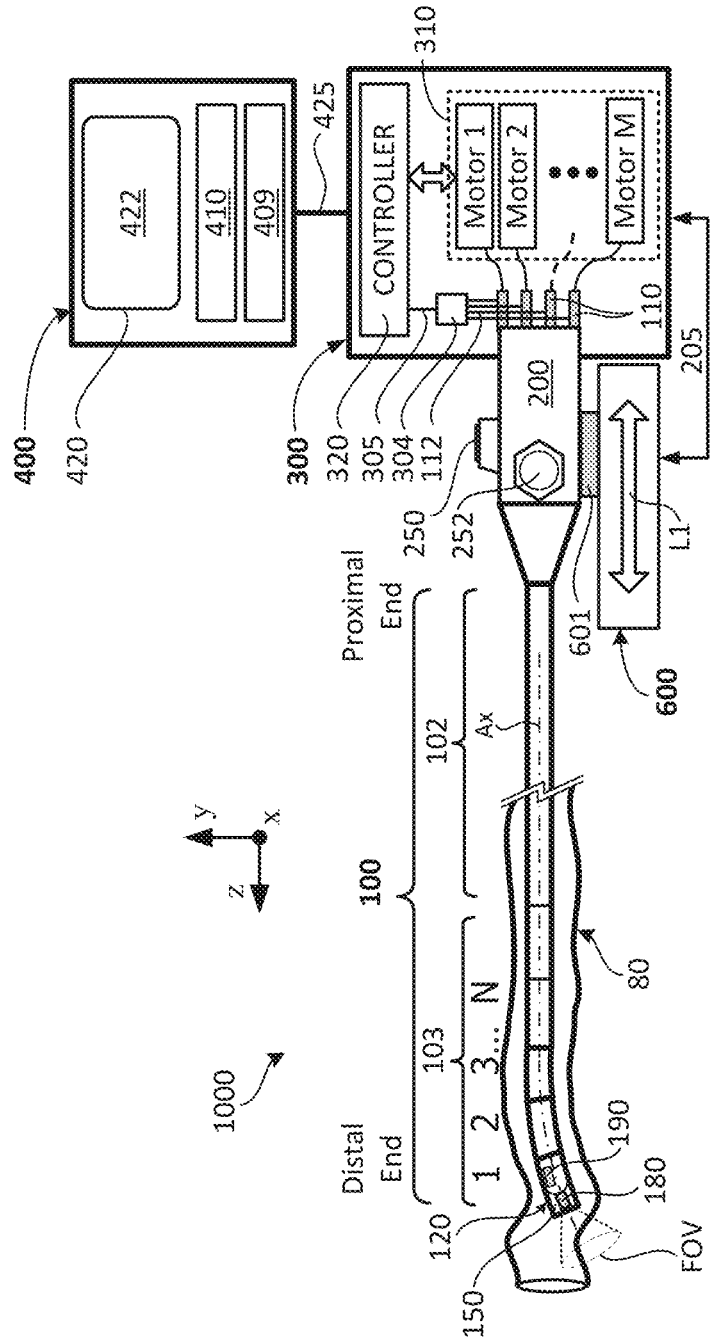
FIG. 1 shows an embodiment of a medical continuum robot (MCR) system moo configured to operate a robotic controlled steerable instrument 100.

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear.

The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into an anatomical lumen 8o (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector sheath, and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

<Medical Continuum Robot (MCR) Having Anti-Twist Feature>

An exemplary configuration of a continuum robot system 1000 having a positioning mechanism 150 is described with reference to FIG. 1 and FIG. 2A-2C. FIG. 1 shows an embodiment of the continuum robot system 1000 configured to operate a robotic controlled steerable instrument 100 (a steerable catheter or endoscope). FIG. 2A—FIG. 2C illustrate in more detail specific structures of the steerable instrument 100 including a non-steerable proximal portion 102, a steerable distal portion 103, and a plurality of control wires 110. The robot system 1000 can be continuum or multi-segment robot configured to adapt the steerable instrument 100 to curved geometries for navigating the steerable catheter through tortuous paths inside an anatomical lumen 80 of a patient's anatomy. The steerable instrument 100 can be used as a steerable catheter, a miniature endoscope, or a flexible needle-guide instrument.

As shown in FIG. 1, a general structure of the continuum robot system 1000 includes a computer system 400 (e.g., a system console), a robotic control system 300, and the steerable instrument 100 which is connected to the control system 300 via a handle 200. In alternate applications or embodiments, the steerable instrument 100 can be connected via the handle 200 to a handheld controller such as a gamepad controller or a portable electronic device such as a smartphone or tablet computer. By convention, the robot system 1000 operates in a three-dimensional (3D) space defined by a 3D Cartesian coordinate system of x, y, z axis. The steerable instrument 100 includes a non-steerable proximal section 102 and a steerable distal section 103 arranged along a longitudinal central axis Ax which is parallel to the z-axis direction. The distal section 103 is divided into multiple bending segments (1, 2, 3 . . . N), and each bending segment is configured to be individually actuated (bent, and/or rotated) by one or more control wires 110.

The bending and/or insertion/withdrawal of steerable instrument 100 (herein generally referred to as "steering") is controlled by a kinematic actuation system comprised of the handle 200, the robotic control system 300, and a controller (e.g., a gamepad controller or the computer system 400). More specifically, the control system 300 generally includes or is connected to a handheld controller and/or a control room computer. The computer system 400 along with suitable software, firmware, and peripheral hardware operated by one or more processors of central processing unit (CPU) 410 represents a generalized controller system used to control steering of the steerable instrument 100. A memory module 409 stores software applications and computer-executable code for operating the continuum robot system 1000 as whole. The computer system 400, the robotic control system 300, and the handle 200 are operably connected to each other by network link or a cable bundle 425. In some embodiments, the control system 300 may be implemented by, or connected to, a handheld controller, such as a gamepad or a portable processing device like a smart phone or a tablet computer. Among other functions, the control system 300 and/or computer system 400 can provide a surgeon or other user with a display screen 422 and a graphical user interface (GUI) through an image display device 420, such as an LCD or OLED display, to enable the user to interact with the steerable instrument 100 and the system as whole.

The handle 200 provides an electromechanical interface between the steerable instrument 100 and the control system 300. For example the handle 200 may provide an interface for mechanical, electrical, and/or optical connections, and a data or digital acquisition (DAQ) system for interfacing the steerable instrument 100 with the control system 300. The handle 200 may also provide an access port 250 that a surgeon or operator may use to insert end effector tools. The handle 200 may also include one or more dials 252 for manually steering of the steerable section 103 of instrument 100. The term "end effector" refers to a working part of a surgical instrument or tool. Endoscopic surgical tools may include clamps, graspers, scissors, staplers, needles, and other similar tools, which serve to manipulate body parts (organs or tissue) during examination or surgery, as it is known to those of ordinary skill in the art. The handle 200 is attachable to a robotic support platform 600 (e.g., a linear stage and/or robotic arm 601) to move the steerable instrument 100 in a linear direction L. The controller system 300 can send control signals to the support platform 600 and/or linear stage 601 via the handle 200 or/or an additional connection 205 such as a network link or cable bundle.

The robotic control system 300 includes an actuator system 310 and a controller 320. The controller 320 may include a proportional-integral-derivative (PID) controller or other digital signal processor (DSP) along with suitable software, firmware and peripheral hardware, as it is known to persons having ordinary skill in the art. PID or DSP-based controllers are generally dedicated integrated circuits; however DSP functionality can also be implemented by other circuits, for example, by using field-programmable gate array chips (FPGAs). The actuator system 310 may include a plurality of actuating motors (or actuators), which are shown in FIG. 1 as Motor 1 through Motor M. In some embodiments M can be equal to the number of control wires 110 necessary for steering the various segments of the distal section 103. In other embodiments, more than one (or all) control wires can be actuated by one motor. The control wires 110 are typically metallic wires anchored at anchor members along the length of the steerable section 103. The robotic control system 300 also includes one or more sensors 304 operatively connected to the control wires 110 and/or to the steerable instrument 100 via electrical wires 112. Sensors 304 can include one or more strain sensor and/or one or more position/orientation sensors which serve to detect and/or measure compressive or tensile forces exerted be the actuator system 310 on the control wires 110. The sensors 304 can output a signal 305 corresponding to the amount of compressive or tensile force (an amount of strain) being applied to each control wire 110 at any given point in time. The signals 305 from the sensors 304 (strain sensor and/or position sensor) for each control wire 110 are fed into the controller 320 to control the actuation of each control wire individually by a feedback control loop. In this manner, each control wire 110 can be actively controlled to implement appropriate shaft guidance for navigating the steerable instrument 100 through intraluminal tortuous paths of a patient's anatomy.

The steerable instrument 100 has an elongated tubular shaft (elongated tubular body) also referred to as a tubular sleeve or tubular guide or tubular sheath. Along the shaft's length, there is at least one working channel 105 extending along (typically inside) the tubular shaft, and a plurality of control wires 110 extending along (typically within) the wall of the tubular shaft. The working channel 105 will be refereed to as a "tool channel" for simplicity. The tool channel 105 allows access for various tools (end effectors) to be delivered from the access port 250 to the distal end of the steerable section 103. The tool channel 105 may also be used for sending or retrieving liquid or gaseous substances (e.g., air or water) to a target area, or for passing optical fibers and/or electric wires necessary for operating the system. Furthermore, the tool channel 105 may be used for removably holding a medical imaging device 180, such as an endoscope camera, a videoscope, or a fiber-based imagining probe. An example of an endoscope camera includes, but is not limited to, a chip-on-tip (COT) camera, such as a camera with a miniature CMOS sensor configured to be arranged at distal tip 120 of the steerable section 103. In addition, one or more electromagnetic (EM) sensors 190 can be provided in the distal tip 120 and/or along the length of the steerable instrument 100. In operation, when the steerable instrument 100 is steered through the anatomical lumen 80, the distal tip 120 is actively bent in one or more directions by the kinematic controller to advance through tortuous anatomies. The remaining segments of the steerable section 103 can be controlled individually or can be operated in a follow-the-leader (FFL) approach. During navigation, the imaging device 180 is inserted into and/or withdrawn from the catheter body through the tool channel 105. When the distal portion of the catheter is actively bent and the imaging device 180 is placed inside the tool channel 105, the tip of the tip of the catheter is free to twist or rotate around the camera. The steering mechanism only bends the catheter, but the twisting or rotation of the catheter around the imaging device is a byproduct of navigation through a tortuous anatomy and friction between the anatomy and the OD of the catheter. To ensure that the imaging device 180 maintains its appropriate position and orientation with respect to the distal tip of the steerable instrument, a positioning mechanism 150 is configured to couple the imaging device 180 to the tool channel 105 at the tip of the catheter.

FIG. 2A, FIG. 2B, and FIG. 2C illustrate further details of the steerable instrument 100, according to an exemplary embodiment of the present disclosure. FIG. 2A is a perspective view of steerable instrument 100 comprising a non-steerable proximal section 102 and a steerable distal section 103 with a positioning mechanism 150 in the tool channel 105 at the distal end thereof. FIG. 2B shows ring-shaped components of the steerable section 103. FIG. 2C shows an actuated state of the steerable instrument 100.

As shown in FIG. 2A, the proximal section 102 is shaped as a tubular shaft with the center axis thereof extending along the Z-axis direction, and a plurality of wire conduits are formed along the wall of the tubular shaft. The distal section 103 includes a plurality of ring-shaped components (also referred herein as guide members 108) arranged distally to the proximal section 102 at a predetermined distance from each other. The distal section 103 includes two bending subsections, a first bending section 103a and a second bending section 103b joined at an inflection point 107. The first bending section 103a includes a plurality of ring-shaped guide members 108a, and the second bending section 103b includes a plurality of ring-shaped guide members 108b.

Along the length of the steerable instrument 100, a plurality of control wires 110 run along the wall of proximal portion 102 and through one or more of the ring-shaped guide members 108 of the distal section 103. At the proximal end of the tubular shaft, all control wires 110 are coupled to individual motors or actuators of the actuator system 310 (as shown in FIG. 1A). In certain embodiments, one or more wires may not be coupled to an actuator, but instead attached to a fixed structure. Along the distal portion 103, the control wires 110 pass through the annular wall of the one or more guide members 108 in a lengthwise direction thereof parallel to the z-axis and are selectively anchored to wire-anchoring components 109. Some control wires 110 are anchored at the inflection point 107 to a first anchor member 109a, and some of the control wires 110 are anchored at the distal end of the steerable section 103 to a second anchor member 109b. The control wires 110 can be metal wires, for example, plano-type wires, stainless-steel wires, or nickel-titanium-alloy (nitinol) wires, shape memory alloy (SMA) wires, or similar structures and/or combinations thereof. The anchor members 109a and 109b have an annular shape with the center axis thereof extending along the z-axis direction similar to the guide members 108. The plurality of control wires 110 are fixedly coupled to the anchor members 109a, and/or 109b, for example, by bonding, pinning, welding, or tightening with screws.

FIG. 2B shows a perspective view of a representative guide member 108b and a representative guide member 108a. Each guide member 108 has an annular shape with the center axis Ax extending along the z-axis direction. Each guide member 108a has six wire conduits 104a, 104b, 104c, 104d, 104e, and 104f on the annular wall thereof to allow passage of corresponding six control wires 110 therethrough (one control wire per wire conduit). Each guide member 108b has three wire conduits 104a, 104c, and 104e extending along the annular wall thereof in the lengthwise direction to allow passage for a corresponding number of control wires 110 to pass and slide therethrough. The wire conduits 104a-104f in each guide member 108a allow passage for 3 control wires 110 which are coupled to the anchor member 109a, and 3 control wires 110 which are coupled to the anchor member 109b. On the other hand, the wire conduits 104a, 104c, and 104e in each guide member 108b allow passage to the corresponding 3 wires to be coupled to the anchor member 109b.

Exemplary movement (steering) of the steerable instrument 100 when the control wires 110 are actively driven to navigate the instrument through a tortuous path is described next. For simplicity, the movement of a single bending segment is explained. As shown in FIG. 2C, a single bending section 103 of steerable instrument 100 includes, from the distal end thereof, an anchor member 109 and a plurality of guide members 108 connected to a tubular shaft of proximal portion 102 by a plurality of control wires 110a, 110b, and 110c. The plurality of wires 110a, 110b, and 110c extend from the proximal end to the distal end along the wall of the tubular shaft and along the wall of each guide member 108 through wire conduits 104a, 104b, and 104c, respectively. At the distal end of the instrument 100, the control wires 110 are fixedly coupled to the anchor member 109; and at the proximal end of the instrument 100, the control wires no are dynamically coupled to corresponding motors or actuators of the actuator system 310. One or more of the control wires 110 are slideable with respect to one or more of the guide members 108 by the action of a corresponding actuator or motor. One of the three control wires 110 (e.g., control wire 110b in FIC. 2C) can be fixed (or mechanically grounded) with respect to guide members 108, and the remaining two control wires 110 (e.g., control wires 110a and 110c in FIG. 2C) are slideable with respect to the wire conduits 104 of the guide members 108.

In bending the steerable instrument 100, each control wire 110 is individually controlled by a respective actuator or motor. For example, in FIG. 2C, while control wire 110b may be fixed or anchored to the anchor member 109 and to the guide members 108, control wire 110a is pulled with a control force F1, and control wired 110c is pulled with a control force F2 (control force F2 is lower than control force F1, in this example). In this manner, the bending section 103 can be bent in a desirable direction, in accordance with a combination of the driving amounts of linear displacement of control wires 110a and 110b. To control the posture of the distal end of the steerable instrument 100 within two degrees of freedom, driving two of the three control wires is sufficient.

While the case of driving two control wires anchored at the distal end of a single bending section has been described above with respect to FIG. 2C, if control wires of all bending sections of FIG. 2A are driven, the postures of each bending section may be independently controlled in accordance with the driving amounts of the individual control wires. Further, a mechanism that actively rotates or twists the wire-driven steerable instrument 100 around its center axis Ax may be additionally provided. For example, to provide an amount of rotation or twisting to the distal end of the steerable instrument, a bending section may be first bent in a desirable direction by driving only one control wire and then the body of the steerable instrument may be rotated by operating a different control wire or by rotating the rotating the handle 200 and control wires included therein.

According to one embodiment, e.g., as shown in FIG. 2A-2C, the steerable instrument 100 may have an outer diameter (OD) of about 0.14 inches, with a distal section 103 being around 2.0 inches in length, and the total length of the instrument 100 being about 24 inches. The anchor members 109 and guide member 108 have wire conduits 104 and a tool channel 105, and are typically constructed from Polyether Block Amide available under the tradename Pebax®. An outer sheath which covers at least part of the instrument 100 and an inner sheath or coating which protects the surface of tool channel 105 can also be made from Pebax. However, other medical-grade plastics or similar composites are also viable, e.g. polyurethane. Typical materials for the tubular shaft of the proximal section 102 also include polyimide and/or polyetheretherketone (PEEK), for example, which can comprise any suitable number of layers. Other materials also include thermoplastic elastomers such as, but not limited to, Pebax®, Fluorinated Ethylene Propylene (FEP); Thermoplastic Polyurethanes such as Pellethane®; silicone biomaterial such as NuSil™ These materials allow for fabrication of flexible, yet torsionally resilient steerable instruments, such as catheters and endoscopes of reduced dimensions. For example, dimensions for another prototype steerable instrument 100 are about 3.3 mm outer diameter (OD), 2.4 mm inner diameter (ID), and about 550 mm of total length.

In another exemplary embodiment, the steerable instrument 100 has been designed with an inner diameter (ID) of about 0.089 inches (2.26 mm) at the distal end of the steerable section 103. In order to provide enough clearance for suction and/or irrigation fluids, the imaging device 180 (a videoscope or camera) has an OD of about 0.061 inches (1.55 mm). This means that there can be a clearance of about 0.028 inches (0.71 mm). According to the present disclosure, it is advantageous to add anti-twist features to the tip of the catheter body and/or to the camera, such that these anti-twist features would act as a means for mechanically interlocking the imaging device with the tip of the catheter body to move together. As used herein, interlocking of two or more components refers to mechanically locking together the two or more components for coordinating functions of the different components. To interlock two or more components refers to mechanically engaging the components with each other by overlapping or by the fitting together of mechanical features such as projections and recesses, keyways and keying tabs, keyholes and pins or keys, etc. In some embodiments, interlocking two or more components may be achieved by pressure fitting such components. FIG. 2A and FIG. 2C show a graphical representation of a positioning mechanism 150 including anti-twist features. It is understood that these anti-twist features would potentially decrease the clearance between the imaging device and the ID of the catheter body, and would potentially reduce the flow rate of fluids during irrigation and/or suction. In addition to a reduction in flow rate, another issue to consider when adding an anti-twist feature is bending stability of the feature. To address the issue of flow rate, the anti-twist feature disclosed herein is made of thin wires or fibers, or a thin metal sheet, and/or thin tubes (e.g., hypotubes). Since the material thickness of the anti-twist feature will be low (thin), the anti-twist feature will only minimally reduce the cross sectional area of the tool channel and thus it is possible to optimize fluid flow. At the same time, the low thickness of the anti-twist feature will increase the possibility of the anti-twist feature bending or collapsing because of reduced stiffness due to lack of material thickness. Thus, if the material thickness is excessively low (too thin), the anti-twist feature could deflect, allowing some twisting of the catheter to occur. Therefore, in consideration of the foregoing factors, the inventor herein has performed various computer assisted design (CAD) simulations of several embodiments of an anti-twist feature to estimate flow rate optimization and appropriate resistance to twisting of the catheter body under various target loads. Details of these simulations are shown in Table 1.

First Embodiment

Figure 3A:
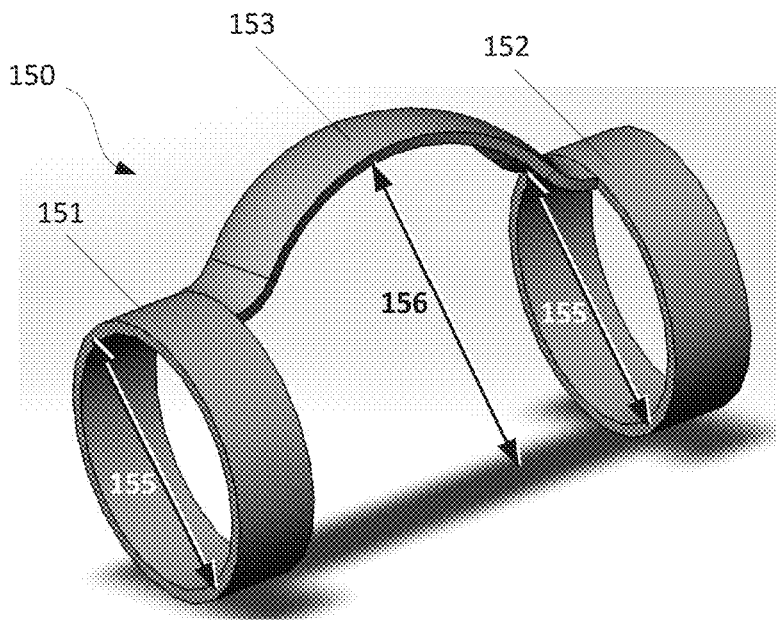
FIG. 3A, FIG. 3B, and FIG. 3C illustrates a positioning mechanism 15o comprising a housing portion (151, 152) and an anti-twist feature implemented by an arcuate tab (153) according to a first embodiment of the present disclosure.
Figure 3B:
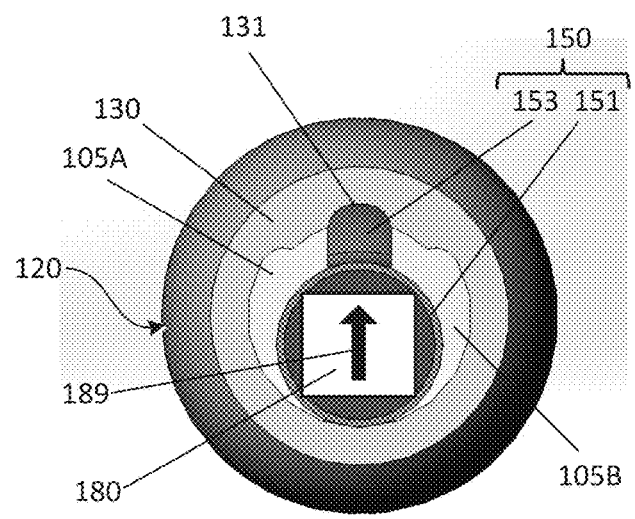
Figure 3C:
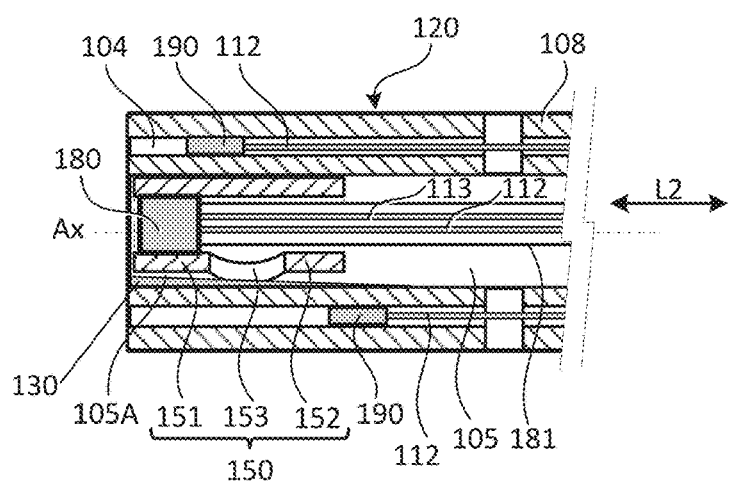

FIG. 3A, FIG. 3B, and FIG. 3C illustrate an anti-twist feature according to a first embodiment of the present disclosure. FIG. 3A and FIG. 3B respectively illustrate perspective and front views of a positioning mechanism 150 according to the first embodiment. FIG. 3C illustrates a cross-sectional view taken in the lengthwise direction (i.e., parallel to the central axis Ax) of a distal tip 120 of steerable instrument 100. According to the first embodiment, a positioning mechanism 150 includes a pair of cylindrical portions 151 and 152 joined by an arcuate tab 153 which protrudes in a radial direction and is arched in the lengthwise direction. The anti-twist feature can be a structure made of polymer and/or metal material. For example, at least the tab 153 can be a polymer tab reinforced by metallic fibers or a metallic tab covered with polymer material, and the cylindrical portions can be of similar or different material. At least one of the cylindrical portions 151 and 152 can be configured to attach to the camera 180, so that the camera 180 can be introduced and secured to the distal end of the tool channel 105. More specifically, the distal tip 120 of the catheter body is configured to be interlocked with the twist-feature which is arranged between the camera 180 and the inner surface of the tool channel 105. In this manner, the anti-twist feature can prevent rotational and lateral movement of the camera relative to the catheter shaft and vice versa. To that end, the distal tip 120 includes an inner sheath or lining or inner surface with engaging features molded inside the distal tip that can engage the anti-twist feature to the tool channel 105. According to the first embodiment, the anti-twist feature has a first cylindrical portion 151 and a second cylindrical portion 152 joined by the tab 153 that arches outward to create an engaging feature that can interlock the camera 180 to the inner surface of the distal tip 120 (i.e., to the surface of the tool channel 105). To provide sufficient area for the flow of fluids through the tool channel 105, the positioning mechanism 150 having an anti-twist feature has a first cross-sectional dimension 155 (a first diameter) smaller than the cross-sectional dimension (diameter) of the tool channel 105, and to secure the anti-twist feature in an interlocked position with respect to the distal tip 120, the anti-twist feature includes the tab 153 with a second cross-sectional dimension 156 (a second diameter) which becomes the same dimension as the cross-sectional dimension (diameter) of the tool channel 105. In most embodiments, the tool channel 105 at the distal tip 120 has an inner sheath or an inner surface with molded features which engage with the tab 153 (or tabs) of the anti-twist feature with a certain amount of pressure.

FIG. 3B shows the distal tip 120, an inner lining or inner sheath 130, the tool channel 105, the camera 180 coupled to the positioning mechanism 150, as seen in the direction from the distal end to the proximal end (i.e., a front view). The camera 180 is fixedly attached to the housing portion of the positioning mechanism 150 (e.g., to one or both the cylindrical portions 151-152) by the camera body 181, and the tab 153 of the anti-twist feature is aligned with a predefined direction 189 (or orientation) of the camera 180. In turn, the anti-twist feature is aligned with a predetermined orientation of the catheter body, by engaging the tab 153 with one or more structures in the inner surface of the tool channel 105 or in the inner sheath 130. For example, in FIG. 3B, the upright ("UP") direction 189 of the camera 180 can be aligned with tab 153 of the anti-twist feature, and the tab 153 is inserted through or engaged with a slot or groove 131 formed in the inner surface of the inner sheath 130. Here, the tab 153 of the anti-twist feature functions as a locking or keying feature (a keying tab) configured to engage with the slot or groove 131 to prevent rotation of the camera 180 within the tool channel 105. That is the slot or groove 131 functions as a keyway configured to receive the keying tab. When the predefined direction 189 is the UP direction (opposite to the direction of gravitational pull), the camera 180 is mounted in a known orientation of the catheter body (i.e., in the upright direction). In this manner, the anti-twist feature will keep the orientation of the camera and distal tip more consistent, and thus allow more intuitive navigation since the camera view will better correspond to navigation inputs, e.g., a right input from the controller will be consistent with a right movement of the catheter tip, and an up input will be consistent with an up movement, etc. throughout the procedure.

FIG. 3C illustrates a cross-sectional view of the camera 180 held within the housing portion of the positioning mechanism 150 and interlocked by anti-twist feature to the distal tip 120 of the catheter body. As shown in FIG. 3C, the positioning mechanism 150 includes the first cylindrical portion 151 and the second cylindrical portion 152 (a housing portion) joined by the longitudinally arcuate tab 153. The first and second cylindrical portions 151 and 152 are dimensioned to have an outer diameter smaller than the inner diameter of the tool channel 105 so as to allow a clearance between the inner sheath 130 and the positioning mechanisms iso. This clearance will ensure that the tool channel 150 maintains sufficient flow for irrigation and/or suction of fluids during certain procedures. The tab 153 is arched or bent outwardly from the first and second cylindrical portions 151 and 152 so at to fit tightly within the inner diameter (ID) of the tool channel 105 with a certain amount of pressure (pressure is provided by a spring effect of the arcuate tab 153). In addition, to facilitate ease of alignment and engagement (coupling) between the anti-twist feature and the surface of tool channel 105, a tapered feature such as chamfered portion of the inner sheath 130 or a molded surface with tapered grooves is formed in the inner surface of the distal tip 120. Tapered grooves can be formed on the surface of the tool channel such that grooves taper in a direction from the distal end to the proximal end. In this manner, the tab or tabs in the anti-twist feature can engage with the tapered grooves, and the camera 180 will maintain its predefined position and/or orientation substantially unchanged even when the distal tip 120 is steered and navigated through tortuous anatomical lumens.

Continuing to refer to FIG. 3C, the distal tip 120 may include one ore more electromagnetic (EM) sensors 190 arranged at a predetermined position and/or orientation with respect to the camera 180, so that the position and/or orientation of the distal tip 120 and/or camera 180 can be actively tracked by, for example, intra-operative imaging and/or intra-operative tracking via an EM tracking system (not shown). Along the length of the steerable instrument 100, one or more electrical cables 112 can be used to electrically connect the camera 180 and/or the EM sensors 190 to electronic circuitry located outside (e.g., in the handle) of the steerable instrument 100. In addition, optical fibers 113 may be used for illumination of the lumen 80 when imaging with camera 180. Therefore, a flexible cable bundle may be attached to the camera body 181; the cable bundle can enclose fibers 113 and/or electrical cables 112 strung together and passed through the tool channel 105. Since the camera 180 is powered by delicate electrical cables 112, and may also include delicate optical fibers 113 (e.g., for illumination), rotation of the camera 180 inside of the tool channel is highly undesirable. However, in order to easily swap a flexible videoscope for one or more end-effector tools, it is advantageous that the camera 180 can be quickly deployed and withdrawn through the tool channel 105 by a linear movement L2 in a direction parallel to the central axis Ax. According to this embodiment, since the tab 153 engages with a groove 131 and provides just enough force to prevent the camera 180 from rotating within the tool channel, the anti-twist feature not only maintains the camera's position and orientation substantially unchanged, but it also protects the electrical and/or optical connections of the videoscope from becoming damaged and/or disconnected, and reinforces the distal tip 120 of the catheter 100. Furthermore, tapered molded features will allow easier registration between the distal tip 120 and the videoscope camera.

Second Embodiment

Figure 4A:
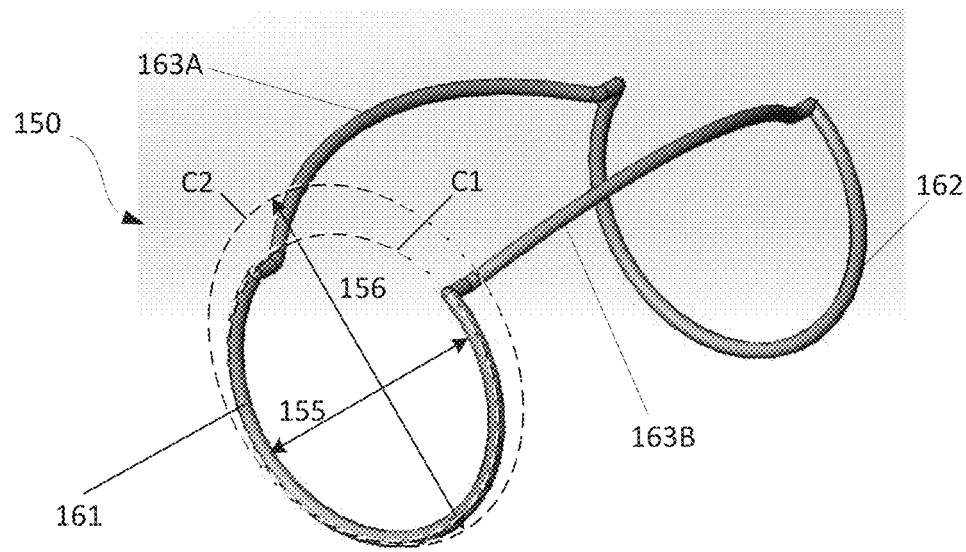
FIG. 4A and FIG. 4B illustrates a second embodiment of the anti-twist feature implemented by a two prong wire (163A, 163B).
Figure 4B:
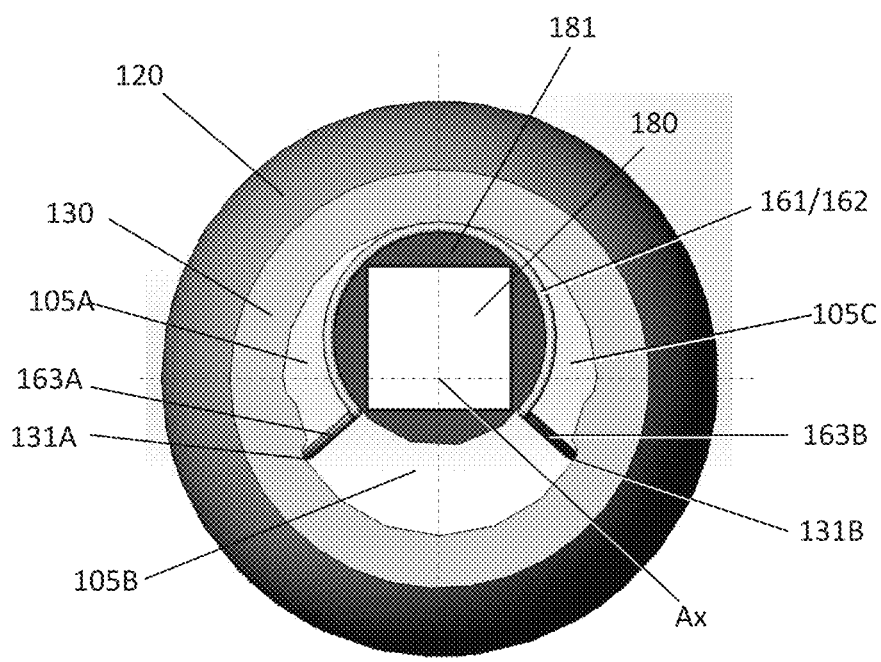

FIG. 4A and FIG. 4B illustrates a second embodiment of the anti-twist feature implemented by a two prong wire. The two-prong wire anti-twist feature is a wire structure comprised a first ring portion 161 and a second ring portion 163 joined by two arched wires 163A and 163B. The first and/or second ring portions 161 and 162 have a first dimension 155 (a first diameter), and one or both of these wire rings are attachable to the camera 180. Also, at least one of the two arched wires 163A and 163B interlocks with mating features molded in the inner surface of distal tip 120 of the steerable instrument 100. More specifically, as shown in FIG. 4B, first and/or second ring portions 161 and 162 are attached to the housing or frame 181 of the camera 180, the first arched wire 163A interlocks with a first groove 131A formed in the inner surface (inner sheath 130), and the second arched wire 163B interlocks with a second groove 131B formed in the inner surface (inner sheath 130) of the tool channel 105. The arched wires 163A and 163B expand radially outwards beyond the diameter 155 of the first and/or second ring portions 161 and 162. Therefore, the arched wires 163A and 163B can provide enough pressure against the inner surface of the tool channel 105 so the camera 180 does not rotate when the catheter body is navigated within the lumen 80. Here, the arched wires 163A and 163B function as a locking or keying feature configured to engage with slots or grooves 131A and 131B (keyways) to prevent camera rotation. To maintain a predefined orientation, the first groove 131A and second groove 131B can be formed at a predetermined angle from each other, and the camera 180 can be arranged with a predetermined direction (e.g., the upright direction) with reference to the first and second groove features formed in the distal tip 120. As shown in FIG. 4B, in this embodiment, the camera 180 is slightly offset with respect to the central axis Ax of the tool channel 105. Nevertheless, by placing the camera 180 slightly offset from the central axis Ax, the anti-twist feature provides anti-rotational stability and ensures enough fluid flow area through sections 105A, 105B, and 105C of the tool channel 105.

Figure 5A:
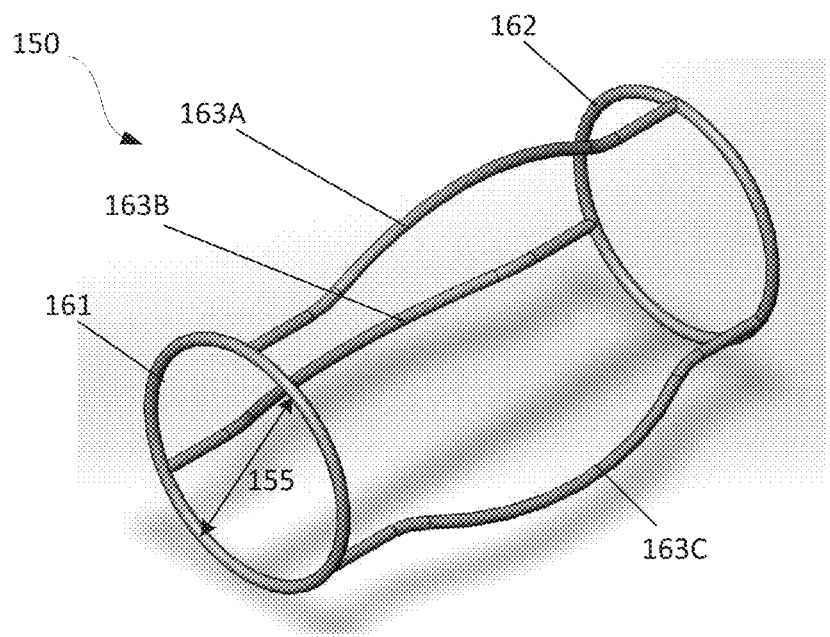
FIG. 5A and FIG. 5B illustrate a modified second embodiment of the anti-twist feature implemented by a three prong wire (163A, 163B, 163C).
Figure 5B:
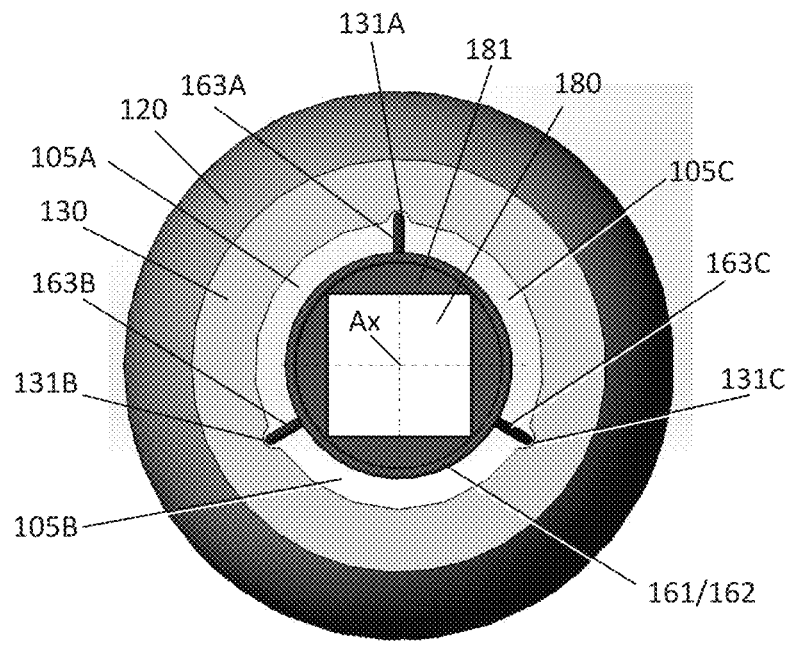

FIG. 5A and FIG. 5B illustrate a modified second embodiment of the anti-twist feature implemented by a three-prong wire structure. Similar to the anti-twist feature of FIG. 4A and FIG. 4B, the anti-twist feature can be implemented by a three-prong wire structure connecting two rings of metallic wire. FIG. 5A shows the positioning mechanism 150 includes a first wire ring portion 161 and a second wire ring portion 162 connected by three arched wires 163A, 163B, and 163C. As shown in FIG. 5B, arched wires 163A, 161B, and 163C can be distributed equidistantly around the wire ring portions 161 and 162. Since the arched wires 163A, 163B, and 163C protrude outwards in a radial direction an approximately equal distance from the ring portions 161 and 162, the camera 180 can be arranged centrally in the tool channel 105. Therefore, a benefit to this design is that the camera 180 can be kept centered (concentric) with the center axis Ax in the inner diameter of the tool channel 105. In this embodiment, sufficient flow area for fluids is provided around the camera 180 and through sections 105A, 105B, and 105C of the tool channel 105. When using relatively thin wire structures, the flow area for fluids provided by the second embodiment (either two-prong wire or three-prong wire anti-twist feature) can be comparatively larger than in other embodiments, as summarized in Table 1 below.

Third Embodiment

Figure 6A:
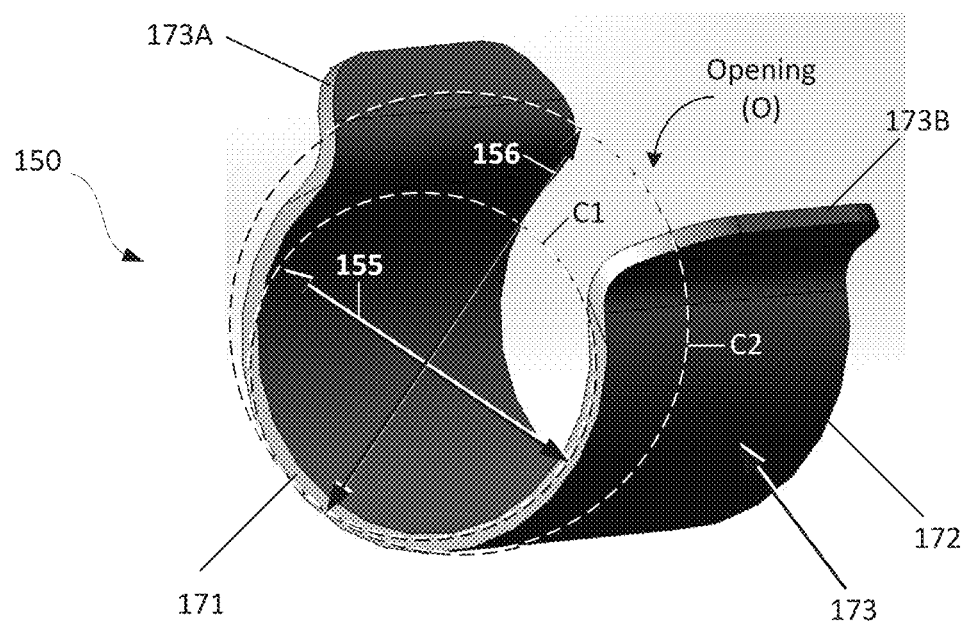
FIG. 6A and FIG. 6B illustrates a third embodiment of the anti-twist feature implemented by a two prong sheet metal structure (173A, 173B).
Figure 6B:
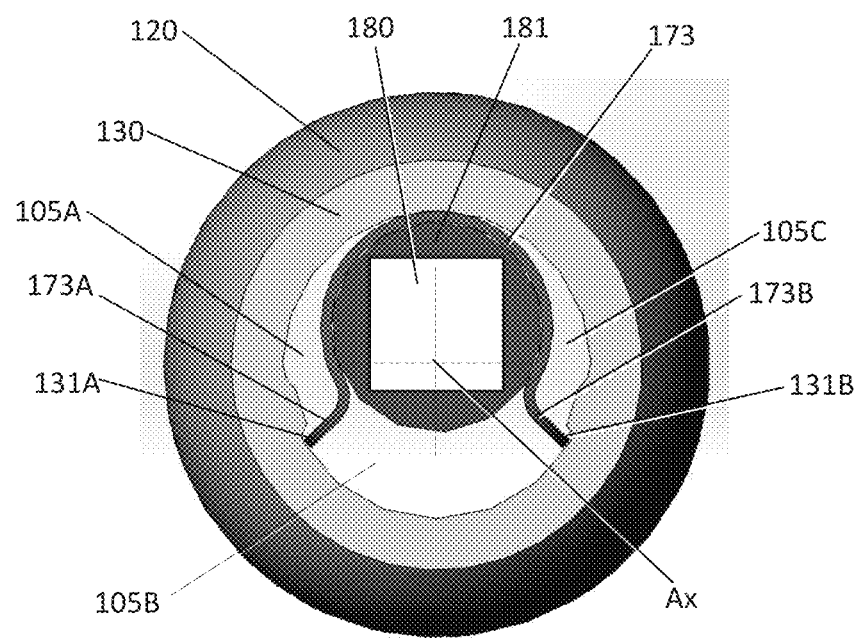

FIG. 6A and FIG. 6B illustrates a third embodiment of an anti-twist feature implemented by a two pronged sheet metal structure. As shown in FIG. 6A, the positioning mechanism 150 includes a housing portion made of a sheet metal structure shaped to form a semi-cylindrical housing 173 having one or more engaging tabs 173A, 173B. The semi-cylindrical housing 173 can be made by rolling a rectangular piece of sheet metal to form a first ring-shaped edge 171 and a second ring-shaped edge 172, and bending outwardly the ends of the rectangular piece of sheet metal to form a first engaging tab 173 and a second engaging tab 173B. The sheet-metal two-pronged structure is similar to the wire structure of FIG. 4A. However, instead of a wire form, the two-prong anti-twist feature design can be made from a single sheet of metal material. The anti-twist feature comprising a two-prong sheet metal may reduce the fluid flow, as compared to the wire-based anti-twist feature, but the housing portion will provide more stability to the camera 180 during navigation. FIG. 6B illustrates a front view (seen from the distal end) of the anti-twist feature arranged in the tool channel 105 at the distal end thereof inside the tool channel 105. In this embodiment, the first engaging tab 173A is inserted (guided) through a groove 131A and the second engaging tab 173B is inserted (guided) through a groove 131B formed in the inner sheath 130 or in the surface of tool channel 105. The camera 180 is arranged in (secured to) the semi-cylindrical housing 173 by the camera body 181 held inside the first ring-shaped edge 171 and/or the second ring-shaped edge 172. In this manner, when the position mechanism 150 is inserted in the tool channel 105, an the anti-twist feature engages with the molded features the camera 180 is slightly offset from the instrument central axis Ax, but the anti-twist feature provides sufficient fluid flow area through sections 105A, 105B, and 105C of the tool channel 105. The anti-twist feature of FIG. 6A-6B is similar to the anti-twist feature of FIG. 4A-4B. Here, the metal sheet for the anti-twist feature can be laser-cut from a conventional hypotube of an appropriate dimension 155, and then mechanically curved to form the engaging tabs 173A and 173B (keying tabs). In alternative implementations, the semi-cylindrical housing 173 can be molded of reinforced polymer material or fabricate by additive manufacturing (3D printed).

Fourth Embodiment

Figure 7A:
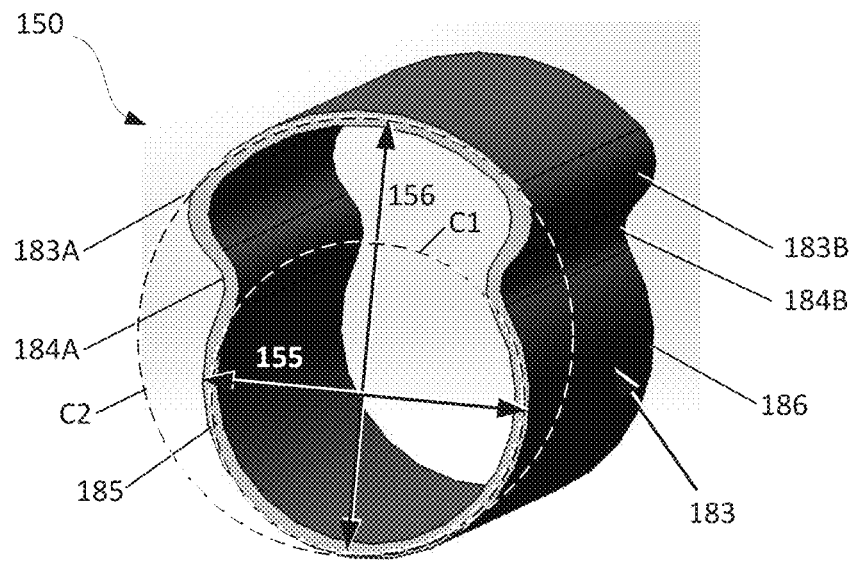
FIG. 7A and FIG. 7B illustrates a fifth embodiment of the anti-twist feature implemented by a modified tube structure having outward curved surfaces (183A, 183B) and inward indentations (184A and 184B) made of sheet metal.
Figure 7B:
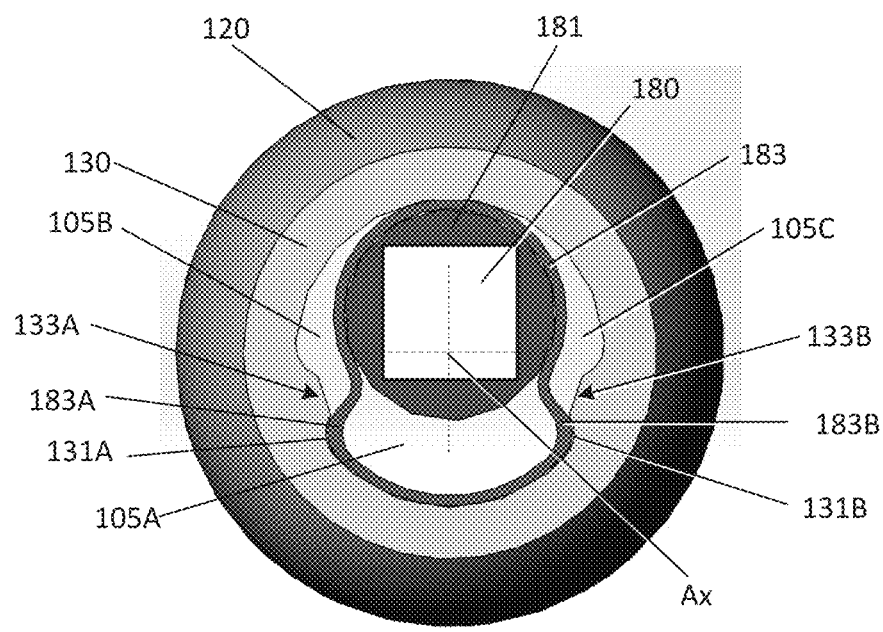

FIG. 7A and FIG. 7B illustrates a fifth embodiment of the anti-twist feature implemented by a modified tube structure. Among the previous embodiments, the two-prong sheet metal structure of FIG. 6A includes two engaging portions (engaging tabs) made of a very thin metal sheet (or other alternative material). These engaging tabs protrude axially outwards from the semi-cylindrical housing 173 and engage with a certain amount of pressure against the molded features inside the tool channel 105 at the distal tip 120. During excessive use of the catheter body, the engaging tabs may become frail and/or the thin edges of the tabs may tend to cut through the inner surface of the catheter wall. Therefore, an alternate design of the anti-twist feature includes a modified tube structure shown in in FIG. 7A. The modified cylindrical structure includes a housing portion formed by a first circular section C1 and anti-twist features made of inward indentations 184A and 184B, and outward curved or convex tabs 183A and 183B. The housing portion C1 has a predetermined length between a distal end surface 185 and a proximal end surface 186. The cross-sectional shape of the proximal and distal end surfaces has a tubular oblong shape with partially collapsed sides bent inwards to form concave ribs or indentations 184A and 184B. In this embodiment, the housing portion includes an irregularly shaped tube 183 having a long diameter 156 and a short diameter 155 perpendicular to each other. The irregularly shaped tube 183 has outward curved portions or convex tabs 183A and 183B, and inward indentations 184A and 184B. The outward curved portions and the inward indentations are substantially symmetric with respect to the long diameter 156 and asymmetric with respect to the short diameter 156. When the positioning mechanism with its anti-twist feature is disposed at the distal end of the catheter body, the outward curved portions and the inward indentations are also asymmetric with respect to the longitudinal axis of the catheter body. The short diameter 155 is smaller than the inner diameter (ID) of the tool channel 105, and the long diameter 156 is approximately equal to or larger than the inner diameter of the tool channel. Here, the convex tabs 183A and 183B include the outward curved portions which function as keying tabs of the anti-twist feature which are pressure fit within the inner diameter of the tool channel 105, when the positioning mechanism is slidably inserted into the tool channel 105.

In one embodiment, this modified tube structure may be formed from a span of sheet metal material similar to that of FIG. 6A, but the tabs can be folded back towards each other to avoid contact of the radial sharp edges with the inner surface of the tool channel. Alternatively, the tube structure 183 can be formed from a short span of a cylindrical metal tube (e.g., a nitinol hypotube) laser-cut to the predetermined length and pressed on opposite sides of the cylindrical tube to form the inward indentations 184A and 184B. As a further alternative the entire anti-twist feature can be extrusion molded or 3D printed, as the other embodiments. Those skilled in the art will also appreciate that the anti-twist feature of this embodiment can have only one inward indentation or more than two inward indentations without losing the anti-twist function.

FIG. 7B shows a front view of the positioning mechanism 150 having an anti-twist feature arranged in the tool channel 105 at the distal tip 120. According to this embodiment, the distal tip 120 includes an inner sheath 130 with molded features in in the form of grooves 131A and 131B (keyways) configured to respectively fit therein the outward curved or rounded tabs 183A and 183B (keying tabs) of the modified cylindrical tube 183. In other words, the tool channel 105 includes two bump portions 133A and 133B which prevent rotation of the positioning mechanism iso. The camera 180 is secured within the housing portion C1 of tube 183 by arranging the camera body 181 inside a first circular section the collapsed tube; a second circular section C2 includes the inward indentations 184A and 184B which create a space (flow areas 105A, 105B, and 105C) between the housing portion and the inner surface of the tool channel 105. In this embodiment, similar to the embodiments of FIGS. 3B, 4B and 6B, the camera 180 is mounted offset from the center axis Ax, and the camera can be mounted in a preferred orientation (e.g., in the UP direction) with respect to the catheter body.

Fifth Embodiment

Figure 8A:
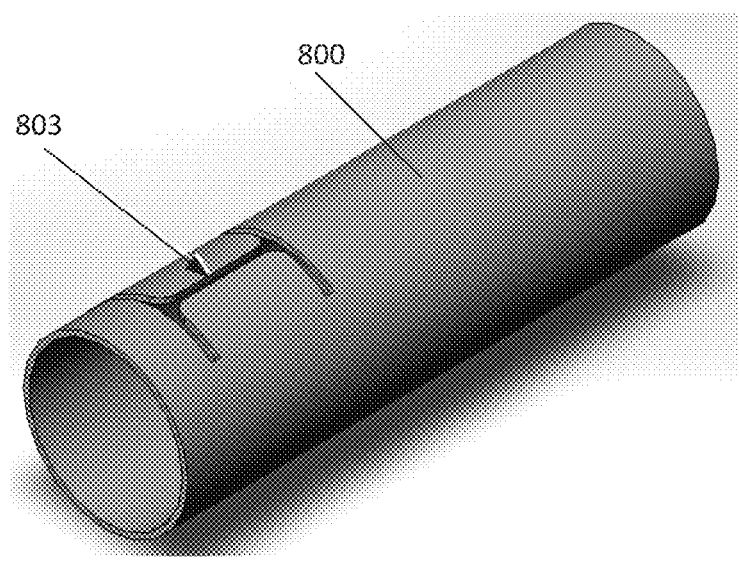
FIG. 8A, FIG. 8B and FIG. 8C illustrates a sixth embodiment of the anti-twist feature implemented by two-pronged linear edges (803A and 803B) of laser-cut hypotube.
Figure 8B:
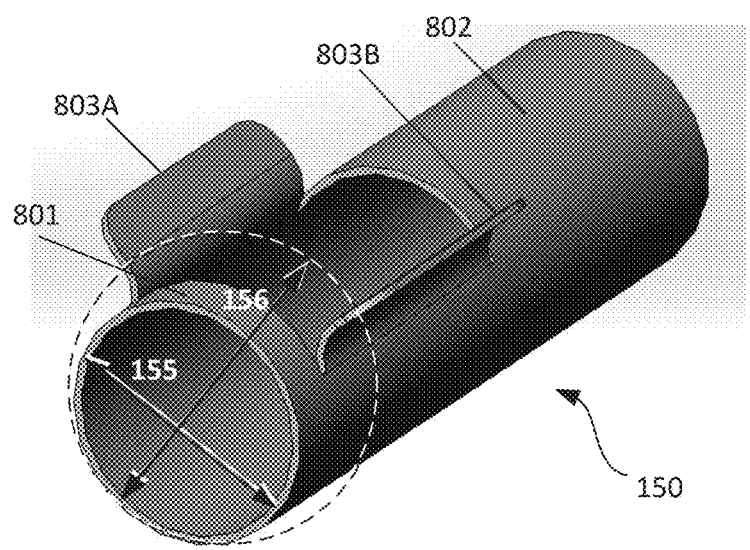
Figure 8C:
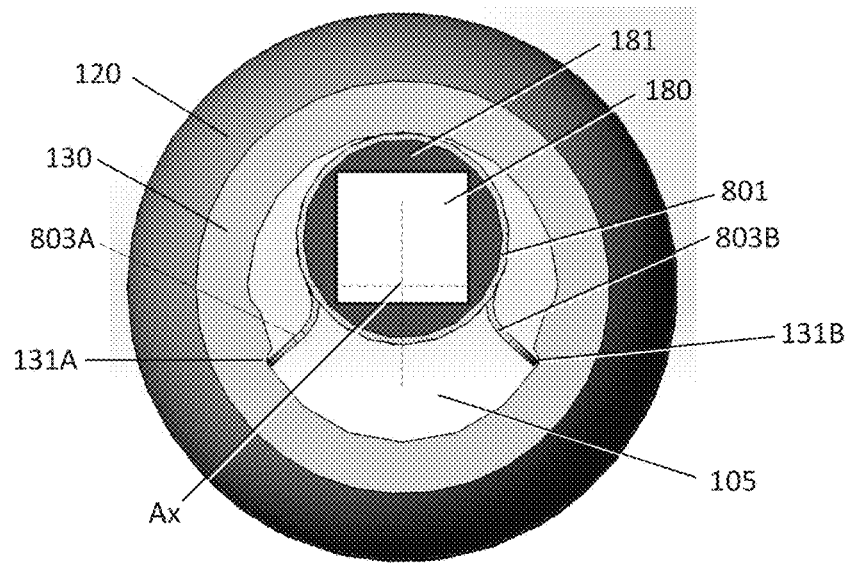

FIG. 8A, FIG. 8B and FIG. 8C illustrate a sixth embodiment of the anti-twist feature implemented by laser cut tube having two-pronged linear edges. FIG. 8A shows a hypotube 800 having a laser-cut H-shaped pattern 803. The H-shaped pattern 803 is preferably a laser-cut pattern made by two parallel circular cuts in the circumferential direction of the tube, and a single linear cut in the lengthwise direction of the tube to join the two parallel circular cuts. These two cuts circumferential and one lengthwise cut form an H-shaped pattern drawn in the circumferential direction such that the two long sides of the "H" wrap around the curved surface of the tube, and the short horizontal part of the "H" runs parallel to the lengthwise direction of the tube axis. FIG. 8B shows the two portions of the tube at each side of the H-shaped cut lifted or bent outward in the radial direction of the tube so as to create a pair of linear tabs 803A and 803B. This pair of linear tabs 803A and 803B protrudes radially from the outer surface of the tube and extends linearly parallel to the tube axis. FIG. 8C illustrates a front view of the distal tip 120 where positioning mechanism 150 is arranged in the tool channel 105 and the anti-twist feature locks the camera 180 to the catheter body to prevent rotation of the camera. Since the positioning mechanism 150 also contacts the inner surface of the distal tip 120, the tube 801 and tabs 803A-803B reinforce the catheter tip and prevent twisting when the catheter bends. To facilitate appropriate engagement of the H-shaped laser cut tube to the tool channel 105, the distal tip 120 has molded features such as a first groove 131A and a second groove 131B (keyways) which are configured to respectively engage with the pair of engaging tabs 803A and 803B (keying tabs). According to this embodiment, the camera 180 is housed at its distal end of the hypotube, the tabs 803A and 803B secure the hypotube to the tool channel 105, and the remainder of the hypotube houses operational electronics, electrical wires, and illumination fibers. The hypotube having the laser-cut "H" pattern on the wall of the tube provides the resulting two parallel tabs of the H pattern that are bent outward in the radial direction to produce two prongs or linear tabs 803A and 803B which engage with the molded features in the tool channel 105 to resist rotation of the camera 180. A benefit of this design is that certain components such as electronics and/or optical fibers can be contained within the hypotube close to the camera chip and additional components are not introduced through the camera shaft, thus maximizing the area for fluid flow. An additional advantage is the use of a well known biocompatible component (i.e., a hypotube) which can result in an economically viable solution to the issue of camera rotation and catheter tip twisting. However, those skilled in the art will appreciate that, as in the other embodiments, the anti-twist feature of this embodiment can be produced of other materials and/or by other processes including, but not limited to, molding or 3D printing based on known polymers.

Sixth Embodiment

Figure 9A:
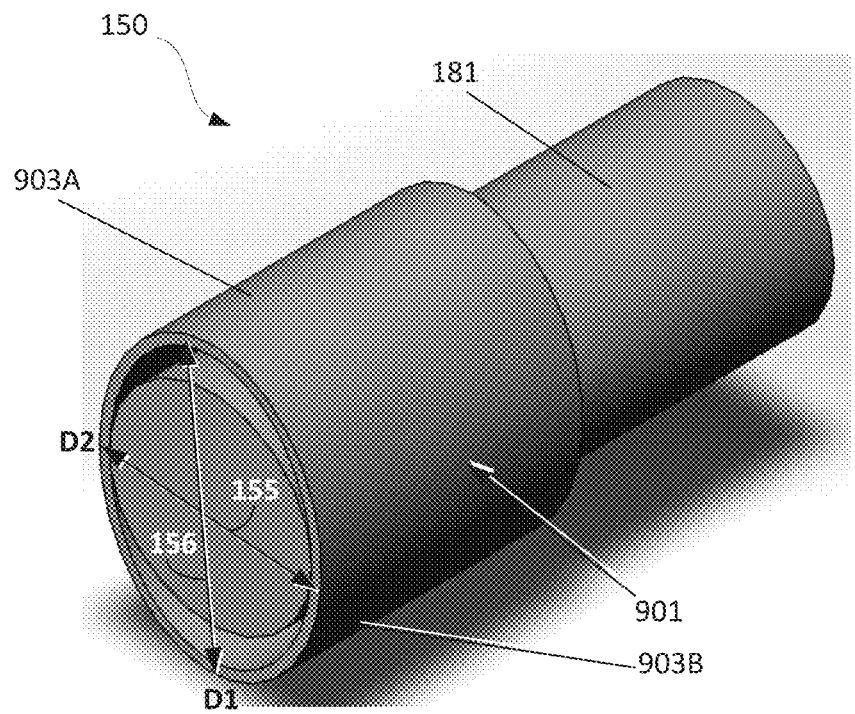
FIG. 9A and FIG. 9B illustrates a seventh embodiment of the anti-twist feature 15 implemented by an elliptical tube structure having outward curved surfaces (903A, 903B) configured to be pressure fit into the tool channel.
Figure 9B:
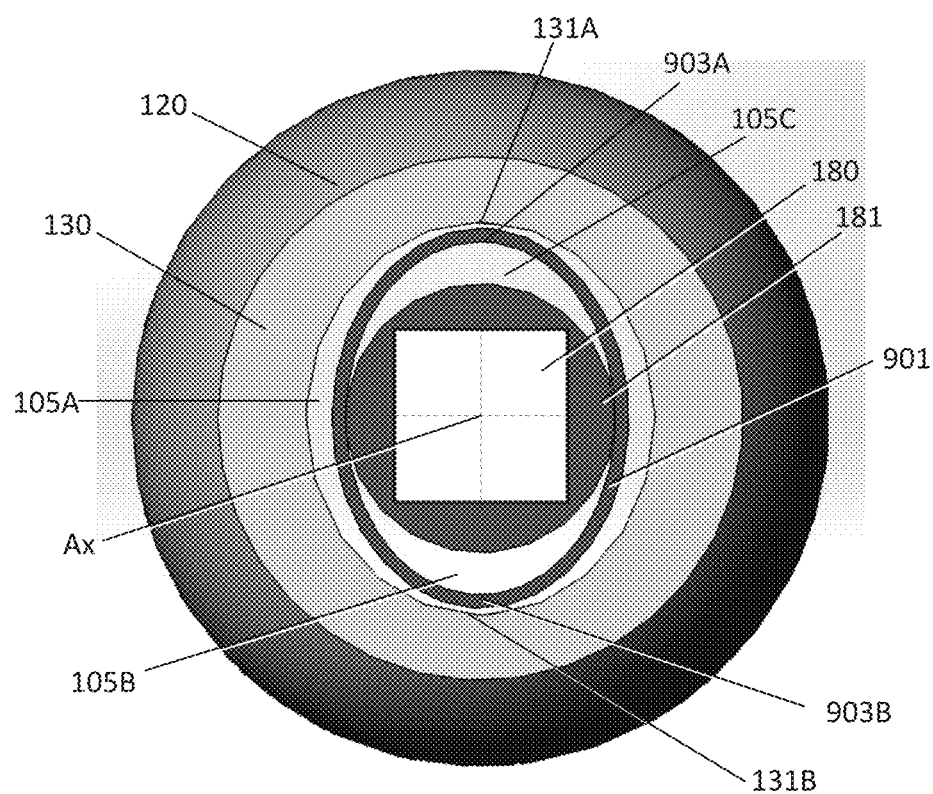

FIG. 9A and FIG. 9B illustrates a sixth embodiment of the anti-twist feature implemented by a tube having an elliptical or oval cross-section (an elliptical tube). As shown in FIG. 9A, an elliptical tube 901 has two curved portions 903A and 903B (corresponding to opposite ends of along a long axis D1 of the elliptical cross-section of tube 901). The camera body 181 is attached to the tube 901 such that the camera 180 is centered at the crossing of a first (long) axis D1 and a second (short) axis D2 of the elliptic cross-section of elliptical tube 901. As used herein, an elliptical tube is a cylinder with a generally elliptical or oval cross section. However, for purposes of manufacturing and assembly, an elliptical tube may have a generally oval or oblong (including flat sided oval) cross-section where a first dimension 156 along the first axis D1 of the cross-section is larger than a second dimension 155 along the second axis D2 of the cross-section. To accommodate the elliptical tube 901 within the tool channel 105, and to prevent rotation of the camera 180, a corresponding slightly elliptical or oval-shaped inner sheath 130 or a molded structure with curved slots, or indentations, or grooves 131A and 131B (keyways) is integrated within the tool channel 105 at very end of the distal tip 120. Curved portions 903A and 903B (corresponding to opposite ends of the elliptical tube 901 along the long axis D1) are arranged in the curved slots, indentations or grooves 131A and 131B respectively to prevent the camera 180 from rotating within the tool channel 105. The use of an elliptical tube 901 would reinforce the distal tip 120 and reduce camera rotation while keeping the camera 180 centered in the tool channel 105. The generally oval or elliptical shape of the tube 901 functions as the housing of the camera body 181 and can provide sufficient area for the flow of fluids through portions 105A, 105B, 105C and 105D of the tool channel 105 surrounding the camera 180 and/or the housing holding the camera body. In this embodiment, the elliptical cylinder 901 (or a tube having a generally oblong cross-section) can be produced from a hypotube compressed on two diametrically opposite sides to form the opposite curved portions 903A and 903B. In other embodiments, the elliptical cylinder 901 can be molded by extrusion (or 3D printed) of well known biocompatible polymers or reinforced polymers (e.g. polymers reinforced by fibers).

Figure 10A:
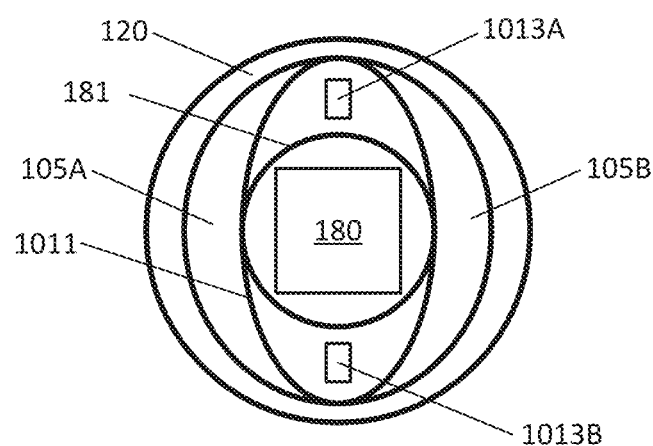
FIG. 10A, FIG. 10B, and FIG. 10C illustrates an eight embodiment of the anti-twist feature implemented by outward curved structures of an oval housing structure configured to support an imaging device centered on the tool channel and to support one or more of illumination optics (1014), illumination electronics (1013), and an auxiliary channel (1014) surrounding the imaging device.
Figure 10B:
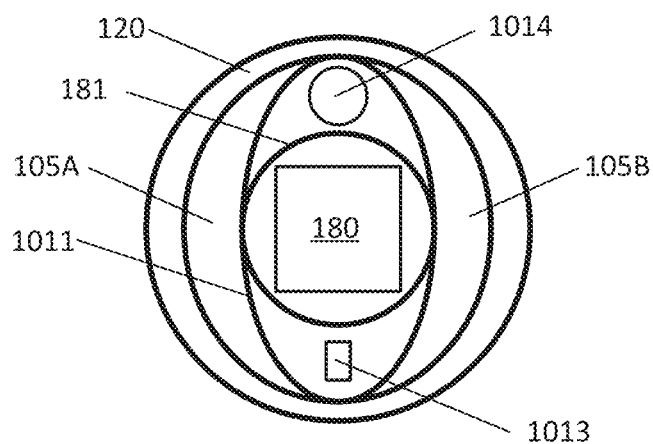
Figure 10C:
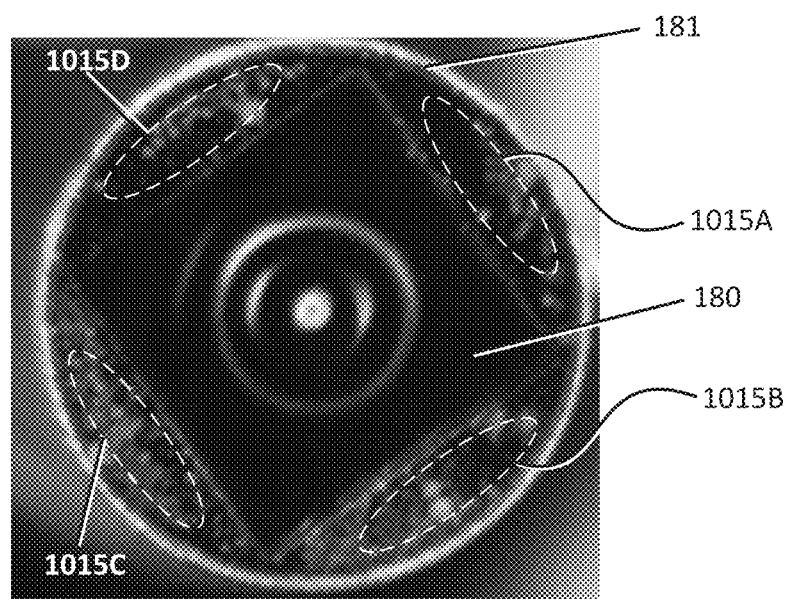

FIG. 10A, FIG. 10B, and FIG. 10C illustrate additional details of the sixth embodiment of the anti-twist feature implemented by an oval housing structure. According to this embodiment, rather than an oval tube attached to the outer surface (chassis or body 181) of the camera, the camera 180, imaging optics 1010 and some electronic components are housed on or around the camera body 181 in an oval-shaped housing 1011. The oval shape of the housing 1011 houses the camera body and still provides an anti-twist feature similar to the embodiment of FIG. 9A-9B. The oval-shaped housing provides room for illumination optics implemented by either optical fibers and/or light emitting diodes (LEDs). FIG. 10C shows a photograph of an actual embodiment for the case of using optical fibers for illumination; in this case, optical fibers are arranged in one or more areas 1015A, 1015B, 1015C and 1015D around the camera 180. According to this embodiment, a large number of optical fibers 1015 can be included next to the camera 180 around a chip-on-tip (COT) structure. A COT camera may include a CMOS chip arranged at the distal tip 120 inside the tool channel 105 of the catheter 100. In the case of fiber-based illumination, the actual illumination source (e.g., an LED or laser) may be housed in a control box outside of the catheter body, and the optical fibers can be strung through the housing shaft.

FIG. 10A shows an embodiment for the case of using electronics-based illumination for the camera 180. In FIG. 10A, first and second LEDs 1013A and 1013B (or an array of LEDs) can be mounted on each side the camera 180 diametrically opposite around the camera body 181 and contained within the housing 1011. Electronic wiring for connecting the LEDs and the camera 180 can be hermetically sealed inside the oval-shaped housing 1011. With two light sources provided diametrically opposite from ach other, the user may use the live view image to identify the camera orientation by recognizing, for example, the brighter areas of the live view image and correlating the location of the two light sources with a predetermined orientation of the camera. For example, the LEDs 1013A and 1013B can have different levels of brightness, and can be aligned with the direction of gravity (gravitational force), so that the user can easily recognize (from the live view image) whether the camera is properly aligned in the up direction or not. In this manner, it is possible to provide the assembly of the anti-twist feature and camera 180 with fewer parts, which would result in good reliability and performance, with an increased flow area for fluids through the tool channel 105.

An advantage of using an oval-shaped housing 1011 is that this housing not only provides a simple anti-twist feature, but it also allows locating either optical fibers and/or one or more small LED's around the camera 180 at the distal end of the tool channel 105. To prevent rotation of the camera, the tool channel 105 can have slightly oval or oblong cross-section similar to the housing 1011.

FIG. 10B illustrates a modified embodiment of the anti-twist feature where the oval housing 1011 provides space for illumination LEDs 1013, and an auxiliary channel 1014. According to this embodiment, the long diameter of the oval-shaped housing 1011 can be designed to fit in the diameter of tool channel 105, while the short diameter of the oval-shaped housing is smaller than the tool channel's diameter and provides areas 105A and 105B within the tool channel for the flow of irrigation and/or suction fluids. The auxiliary channel 1014 can be used for passing other fluids (e.g., contrast agents) and/or auxiliary tools. Therefore, this configuration allows for providing illumination, irrigation and suction fluids flow, and anti-twisting features at the same time.

Also, the single side illumination and auxiliary channel arranged diametrically opposite to each other would allow for an embodiment where the user can identify the camera orientation by observing the live view image. More specifically, when illumination is provided at only one side of the camera, the user can observe the live view image and identify the camera orientation by seeing the area of the live view image with the higher amount of illumination. Moreover, the position of the auxiliary fluid channel 104 can be identified from the live view image (opposite to the brightest area of the image) and intuitively used for irrigation, suction, or tool delivery too.

Modified Sixth Embodiment

Figure 11A:
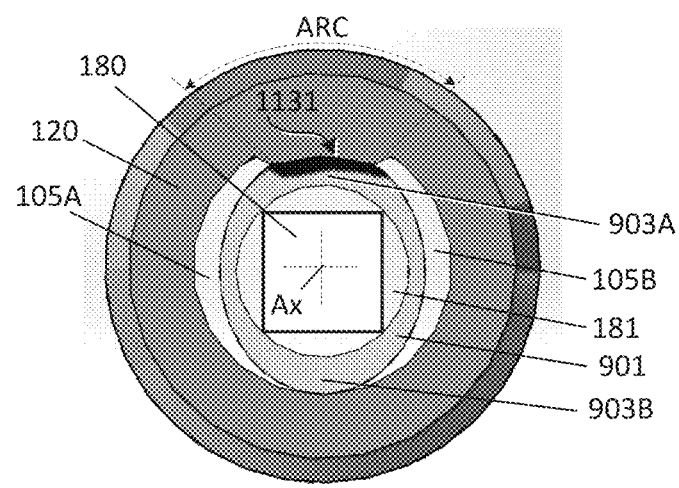
FIG. 11A shows a distal tip 120 with a built-in single bump 1131 configured to prevent rotation of the camera 180.
Figure 11B:
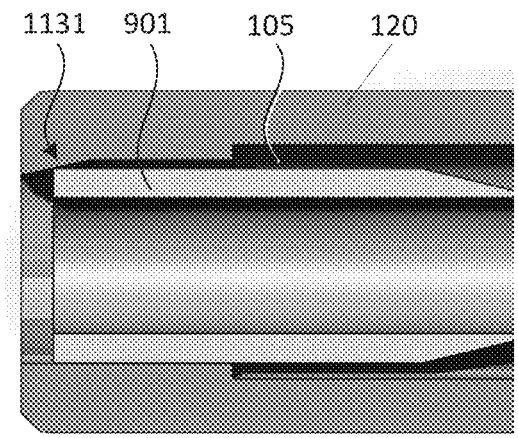
FIG. 11B shows a sectional view of the distal tip 120 taken in the lengthwise direction of the catheter 100.

FIG. 11A, FIG. 11B, FIG. 11C, FIG. 12A, FIG. 12B, FIG. 13A, and FIG. 13B illustrate a modified sixth embodiment of the anti-twist feature implemented by an elliptical tube 901 and locking features in the form of one or more bumps built-in within the tool channel 105 at the distal end of the catheter 100. FIG. 11A shows the distal tip 120 with a built-in single bump 1131 configured to prevent rotation of the camera 180 and/or twisting of the catheter tip. In FIG. 11A, the bump 1131 is a raised surface that protrudes from the inner surface of the tool channel 105 so as to reduce the diameter of an arc (ARC) of about 5 to 20 degrees of the circular surface of tool channel 105. The bump 1131 is shaped as an upturned arched surface that tapers in the direction from the distal end towards the proximal end, as shown in FIG. 11B. To avoid rotation of the camera 180, the bump 1131 includes a slightly curved surface (a recess) configured to receive a first curved portion (portion 903A) of the tube 901. Also, a second curved portion (portion 903B) of the tube 901 contacts the surface of the tool channel 105 with a certain amount of pressure. This reinforces the distal tip 120 and prevents twisting thereof during steering of the catheter. FIG. 11B shows a sectional view of the distal tip 120 taken in the lengthwise direction of the catheter 100. As shown in FIG. 11B, the tapered bump 1131 also serves to stop the camera 180 from exiting through the distal end of the distal tip 120. Specifically, as the camera 180 is mounted on the tube 901 and inserted into the tool channel 105, the tube 901 is locked between the raised surface of bump 1131 and a diametrically opposing section of the surface of the tool channel 105. Due to the elliptical or oval cross-section of the tube 901 and the non-symmetric arrangement of the bump 1131 within the tool channel, the camera 180 can be locked slightly offset from the catheter central axis Ax. Nevertheless, the tool channel 105 still remains with sufficient clearance for fluid flow through areas 105A and 105B of the channel 105 surrounding the tube 901.

Figure 11C:
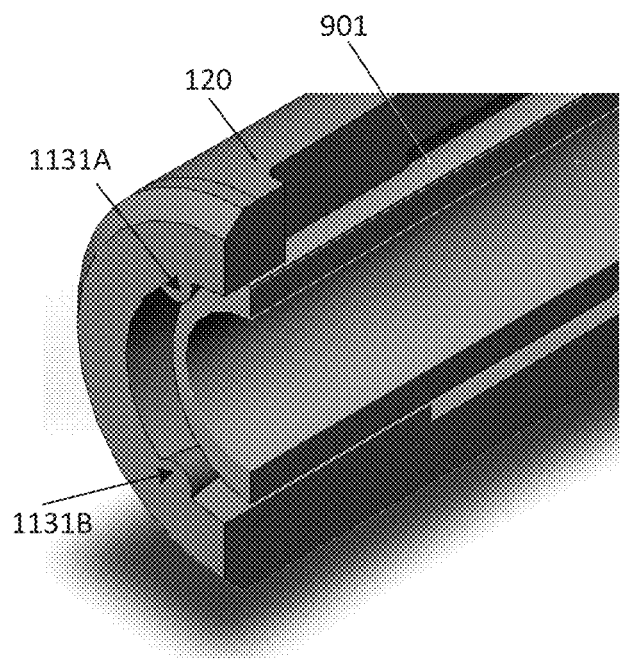
FIG. 11C shows an embodiment where the tool channel 105 can be provided with a plurality of bumps at the distal end of distal tip 120.

FIG. 11C shows an embodiment where the tool channel 105 can be provided with a plurality of bumps at the distal end of distal tip 120. In FIG. 11C, a perspective rendering of the distal tip 120 shows the elliptic tube 901 can be locked by at least a first bump 1131A and a second bump 1131B. In this case, bumps 1131A and 1131B include substantially cylindrical (or half cylindrical or conical) ribs with its diameter protruding towards the central axis, and tapering in the lengthwise direction from the distal to proximal end, similar to the bump 1131 shown in FIG. 11B. Since the tube 901 has an elliptic or oval cross-section, to provide sufficient area for the flow of fluids through the tool channel 105, the positioning mechanism 150 has a first cross-sectional dimension 155 (a first diameter) smaller than the cross-sectional dimension (diameter) of the tool channel 105, and to secure the tube 901 in an interlocked position with respect to the distal tip 120, the tube 901 has a second cross-sectional dimension 156 (a second diameter) which becomes the same dimension as the cross-sectional dimension (diameter) of the tool channel 105. The surfaces of the tube at both end of the second cross-sectional dimension 156 are arranged substantially in contact with the surface of the tool channel and in between two or more bumps 1131. In some embodiments, the outer surface of tube 901 can be provided with at least one outfacing curved recess configured to align and engage with at least one of the bumps 1131A or 1131B, so that the camera 180 does not rotate with respect to the distal tip 120 of the catheter 100.

FIG. 12A through FIG. 13B show certain advantages of the anti-twist feature according to the modified sixth embodiment where one or more bumps are respectively at a maximum material condition and at a minimum material condition. FIG. 12A is a front view as seen from the distal end of the catheter 100, and FIG. 12B is a sectional view taken along section AA of the catheter body in the lengthwise direction. In FIG. 12A and FIG. 12B, the distal tip 120 of the catheter 100 is provided with a plurality of bumps 1131A, 1131B, 1131C, and 1131D arranged inside the surface of tool channel 105 distributed asymmetrically around the central axis Ax. In this case, an anti-twist feature includes a first bump 1131A, a second bump 1131B, a third bump 1131C and a fourth bump 1131D configured to lock the tube 901 in a fixed position and orientation with respect to the catheter body. Each bump 1131 is at its maximum material condition and tappers in a direction from the distal end toward the proximal end at an angle β1. At the maximum material condition of the bumps 1131A to 1131D, the tube 901 is inserted from the proximal end so as to be locked against one or more of the plurality of bumps. The elliptical tube 901 can be guided to be locked between two or more burns by the user observing the live view image during insertion. In other embodiments, the elliptical tube 901 can be provided with one or more tapering recesses 904 on the outer surface thereof, and these one or more tapering recesses 904 can be used by the user to lock the tube 901 to one of the bumps 1131, such that the imaging device 180 remains fixed at a position and/or orientation. After insertion, the camera 180 remains inside the channel 105 at a distance 1220 away from the distal end of the catheter. In the arrangement shown in FIG. 12A-12B, the bumps 1131A to 1131D ensure that the camera 180 can acquire a FOV image of at least 120 degrees, and also prevent the camera 180 from protruding beyond the distal end of the catheter.

FIG. 13A is a front view as seen from the distal end of the catheter 100, and FIG. 13B is a sectional view taken along section BB of the catheter body in the lengthwise direction. In FIG. 13A and FIG. 13B, the distal tip 120 of the catheter 100 is provided with a plurality of bumps 1131A, 1131B, 1131C, and 1131D arranged inside the tool channel 105 asymmetrically around the central axis Ax. In this case, the locking feature includes a first bump 1131A, a second bump 1131B, a third bump 1131C and a fourth bump 1131D. Each bump is at its minimum material condition and tappers in a direction from the distal end to the proximal end at an angle β2 smaller than β1. At the minimum material condition of the bumps 1131A to 1131D, the tube 901 is inserted from the proximal end so as to be locked against one or more of the plurality of bumps, so that the camera 180 remains inside the channel 105 a distance 1320 away from the distal end of the catheter. In this case, the bumps 1131A to 1131D still prevent the camera 180 from protruding beyond the distal end of the catheter, but after certain number of procedure the camera 180 may become dislodged from the bumps 1131a-1131D and could protrude through beyond the distal end of the catheter. Therefore, it will be necessary to give careful consideration to design the bumps 1131A to 1131D with a balance between maximum and minimum material conditions, so as to allow the camera to be locked in an anti-rotating position and with an appropriate filed of view.

As used herein, maximum and minimum material conditions of the anti-twist features are considerations of material hardness or size or other related parameter used when designing the features. The engagement of the features to the oval camera body has to be secure when the features are at their largest and smallest. Due to the designed interference between the camera and the catheter features, the camera will end up closest to the distal end of the catheter tip at the minimum material condition, and farther back at the maximum material condition. However, at the maximum material condition, the camera cannot be so far back that its field of view is obstructed. Also, at the maximum material condition, all intended instruments to be used with the catheter must pass through the locking features built inside the surface of tool channel 105.

<Table 1: Comparison of Anti-Twist Features>

Important design considerations for the anti-twist feature include, but are not limited to, rotational stability of the camera while navigating the instrument through tortuous paths, optimized area for fluid flow, avoidance of sharp edges or punctured components that could cause deformation or damage of the MCR, minimization of cost, reduction of overall size, and keeping the camera in a substantially fixed position/orientation either centered or within a tolerable offset distance from the tool channel axis. Table 1 below outlines how each design/embodiment compares to the others in fulfilling one or more of the above considerations.

TABLE 1

|  | 2 Prong Wire | 3 Prong Wire | Tab | 2 Prong Sheet Metal | Modified Sheet Metal Oval | 2 Prong Laser Cut Tube (H) | Oval Tube |
| --- | --- | --- | --- | --- | --- | --- | --- |
| Avg. Flow Area | 2.1 mm$^2$ | 1.7 mm$^2$ | 1.8 mm$^2$ | 1.9 mm$^2$ | 1.8 mm$^2$ | 2.1 mm$^2$ | 1.6 mm$^2$ |
| Sharp Edges | Moderate | Moderate | Low | High | Low-Moderate | High | Low-Moderate |
| Est. Mfg. Cost | High | High | Moderate | Moderate | Moderate | Moderate | Low |
| Rotational Stability | <1 μm | <1 μm | <0.1 μm | <0.1 μm | <0.1 μm | <1 μm | <1 μm |
| Concentric with Inst. Axis | No | Yes | No | No | No | No | Yes |

The MCR has a removable camera that interlocks with the catheter tip via anti-twist features without increasing the overall profile of the catheter body. The anti-twist features will keep the orientation of the camera and distal tip more consistent, and thus allow more intuitive navigation since the camera field-of-view will better correspond to navigation inputs, i.e., right will be right, and up will be up, etc. throughout the procedure. The features will also still allow suction and irrigation to be performed without having to remove the camera. This feature is also important because, during image guidance, the gap between the camera and the catheter inner wall is also used to supply/remove fluids (e.g., water or gas) to clean bodily substances (e.g., mucus) blocking the camera view.

The various embodiments of anti-twist features disclosed herein are described as applicable to a Medical Continuum Robotic (MCR) catheter system including a flexible videoscope. However, the present disclosure is not limited thereto. Any endoscopy system that needs to maintain the endoscope image substantially unchanged can implement and benefit from the anti-twist features disclosed herein.

Some considerations for optimizing the advantageous effects of the anti-twist feature disclosed herein include: The distal tip of the catheter will incorporate features that can be molded into it, and will act as an interlock between the distal tip and the flexible videoscope; the molded features will engage with the anti-twist feature to interlock the distal tip with the videoscope; the molded features can be tapered/drafted to allow easier registration (coupling) between the tip and the videoscope; the molded features are designed to minimally decrease lumen size/cross sectional area of the tool channel; the anti-twist feature can be permanently attached to the distal end of the videoscope; the anti-twist feature on the videoscope will be stable enough to provide sufficient rotational stability to maintain image orientation substantially unchanged; the cross sectional area and overall volume of the anti-twist feature are minimized to optimize fluid flow without removing the videoscope imaging device.

<Software Related Disclosure>

At least certain aspects of the exemplary embodiments described herein can be realized by a computer of a system or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. The computer may include various components known to a person having ordinary skill in the art. For example, the computer may include signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

MODIFICATIONS AND/OR COMBINATIONS OF EMBODIMENTS

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. All embodiments can be modified and/or combined to improve and or simplify the anti-twist feature as applicable to specific applications. The scope of the following claims is to be accorded the broadest interpretation so as to encompass all such modifications and equivalent structures and functions.

What is claimed is:

1. A steerable catheter, comprising:
a catheter body having a tool channel extending from a proximal end to a distal end along a longitudinal axis of the catheter body;
a positioning mechanism configure to be coupled with an imaging device and to be slidably inserted into and/or withdrawn from the distal end of the catheter body through the tool channel,
wherein the catheter body has an anti-twist feature configured to interlock the catheter body and the imaging device at the distal end of the catheter body so as to prevent rotation of the imaging device within the tool channel and/or prevent twisting of the distal end of the catheter body,
wherein the anti-twist feature includes one or more bumps that are molded portions of the catheter body protruding radially inward from the surface of the tool channel and tapering in the lengthwise direction from the distal end toward the proximal end of the catheter body, and
wherein the positioning mechanism includes a housing portion made of an elliptical tube attachable to the imaging device, wherein the elliptical tube is configured to be pressure fit against one of the one or more bumps and against inner surface of the tool channel at the distal tip of the catheter body.

2. The steerable catheter according to claim 1,
wherein the catheter body includes a proximal section attachable to an actuator unit and a distal section insertable into an anatomical lumen, the catheter body having a plurality of control wires arranged along a wall of the catheter body and configured to transfer an actuating force from the actuator unit to the catheter body so as to steer at least part of the distal section of the catheter body.

3. The steerable catheter according to claim 2, wherein, at the distal end of the catheter body, the tool channel includes one or more keyways configured to be interlocked with the anti-twist feature such that a position and/or orientation of the imaging device coupled to the positioning mechanism remains substantially unchanged with respect to the distal end of the catheter body when the distal section of the catheter body is steered by the actuating force.

4. The steerable catheter according to claim 3, wherein the positioning mechanism includes a housing portion attachable to the imaging device and the anti-twist feature includes one or more keying tabs configured to fit into at least one of the one or more keyways of the tool channel.

5. The steerable catheter according to claim 4, wherein, at the distal end of the catheter body, the tool channel includes a cylindrical surface that extends through the distal portion in a lengthwise direction, and the one or more keyways include linear keyways formed in the lengthwise direction on the cylindrical surface of the tool channel,
wherein the one or more keying tabs of the anti-twist feature include one or more arcuate tabs protruding radially from the housing portion and extending in the lengthwise direction of the tool channel, and
wherein, when the positioning mechanism coupled to the imaging device is inserted into the tool channel, at least one arcuate tab of the anti-twist feature fits into one of the linear keyways formed in the cylindrical surface of the tool channel thereby interlocking the imaging device to the catheter body.

6. The steerable catheter according to claim 4, wherein, at the distal end of the catheter body, the tool channel includes a surface made of an inner lining or an inner sheath,
wherein the one or more keyways of the tube channel include one or more molded grooves formed in the lengthwise direction on the surface of the tool channel,
wherein the one or more molded grooves are tapered in the lengthwise direction from the distal end towards the proximal end of the tool channel to facilitate engagement between the one or more keying tabs of the anti-twist feature and the surface of the tool channel, and
wherein the engagement between at least one of the one or more molded grooves with at least one of the one or more keying tabs enable registration between the distal end of the catheter body and the imaging device.

7. The steerable catheter according to claim 4, wherein the one or more keying tabs of the anti-twist feature are configured to fit into at least one of the one or more keyways formed on the surface of the tool channel at the distal end of the catheter body such that the imaging device is arranged concentric with the longitudinal axis of the tool channel.

8. The steerable catheter according to claim 4, wherein the one or more keying tabs of the anti-twist feature are configured to fit into at least one of the one or more keyways formed on the surface of the tool channel at the distal end of the catheter body such that the imaging device is arranged radially offset with respect to the longitudinal axis of the tool channel.

9. The steerable catheter according to claim 4, wherein the tool channel includes a cylindrical surface that extends through the distal portion in a lengthwise direction,
wherein the housing portion of the positioning mechanism has a first cross-sectional dimension which is smaller than a diameter of the cylindrical surface of the tool channel,
wherein the one or more keying tabs of the anti-twist feature include one ore more arcuate tabs or wires extending radially outward from the housing portion to a second cross-sectional dimension of the anti-twist feature, and
wherein the second cross-sectional dimension of the anti-twist feature is approximately equal to or greater than the diameter of the cylindrical surface of the tool channel.

10. The steerable catheter according to claim 4, wherein, at the distal end of the catheter body, the tool channel has a circular cross-section of a predetermined diameter, and the one or more keyways are linear grooves formed on the surface of the tool channel,
wherein the housing portion of the positioning mechanism includes a portion of a cylindrical hypotube, and a diameter of the cylindrical hypotube is smaller than the predetermined diameter of the circular cross-section of the tool channel,
wherein the cylindrical hypotube includes a laser cut pattern which provides one or more linear tabs protruding radially from the housing portion, and the linear tabs extend in the lengthwise direction parallel to the longitudinal axis of the catheter body,
wherein the one or more keying tabs of the anti-twist feature include the one or more linear tabs of the laser cut pattern, and
wherein the one or more linear tabs of the hypotube are configured to fit into the linear grooves formed on the surface of the tool channel.

11. The steerable catheter according to claim 4, wherein, at the distal end of the catheter body, the tool channel has a circular cross-section which defines an inner diameter,
wherein the housing portion of the positioning mechanism includes an elliptic cylinder having a first diameter and a second diameter, wherein the second diameter is smaller than the inner diameter of the tool channel, and
wherein the one or more keying tabs of the anti-twist feature include the two curved portions corresponding to the first diameter of the elliptic cylinder which are pressure fit within the inner diameter of the tool channel.

12. The steerable catheter according to claim 4, wherein, at the distal end of the catheter body, the tool channel has a circular cross-section having an inner diameter,
wherein the housing portion of the positioning mechanism includes a semi-cylindrical tube having an opening in the lengthwise direction, and the one or more keying tabs of the anti-twist feature include one or more linear tabs formed by portions of the semi-cylindrical tube protruding radially outwards from the semi-cylindrical tube and extending in the lengthwise direction, and
wherein the one or more linear tabs are configured to be pressure fit within the inner diameter of the tool channel.

13. The steerable catheter according to claim 4,
wherein, at the distal end of the catheter body, the tool channel has a circular cross-section having an inner diameter,
wherein the housing portion of the positioning mechanism includes an irregularly shaped tube having a long diameter and a short diameter perpendicular to each other, wherein the irregularly shaped tube has outward curved portions and inward indentations, the outward curved portions and the inward indentations are symmetric with respect to the long diameter and asymmetric with respect to the short diameter,
wherein the short diameter is smaller than the inner diameter of the tool channel and the long diameter is approximately equal or larger than the inner diameter of the tool channel, and
wherein the one or more keying tabs of the anti-twist feature include the outward curved portions which are pressure fit within the inner diameter of the tool channel.

14. The steerable medical catheter according to claim 4,
wherein, at the distal end of the catheter body, the tool channel has a circular cross-section having an inner diameter,
wherein the housing portion of the positioning mechanism includes an oval-shaped tube having a long diameter and a short diameter, wherein the short diameter of the oval-shaped tube is smaller than the inner diameter of the tool channel,
wherein the one or more keying tabs of the anti-twist feature include two outward curved portions corresponding to the long diameter of the oval-shaped tube, and the two outward curved portions are pressure fit within the inner diameter of the tool channel, and
wherein the oval-shaped tube is configured to support the imaging device substantially concentric with the longitudinal axis, and support one or more of illumination optics, illumination electronics, and an auxiliary channel surrounding the imaging device.

15. The steerable catheter according to claim 4,
wherein the one or more keying tabs of the anti-twist feature are molded features formed on the surface of the tool channel, and
wherein the molded features engage with the one or more keying tabs of the anti-twist feature thereby decreasing an inner diameter of the tool channel.

16. The steerable catheter according to claim 2,
wherein, when the distal section of the catheter body is steered by the actuating force, the distal end of the catheter body is moved within the lumen without changing a position and/or orientation of the imaging device with respect to the tool channel.

17. The steerable catheter according to claim 2,
wherein the one or more bumps are configured to be interlocked with the anti-twist feature such that a position and/or orientation of the imaging device coupled to the positioning mechanism remains substantially unchanged with respect to the distal end of the catheter body when the distal section of the catheter body is steered by the actuating force.

18. The steerable catheter according to claim 1,
wherein the housing portion of the positioning mechanism is permanently attached to the imaging device, and
wherein the imaging device is a camera arranged at a distal end of a flexible videoscope.

19. The steerable catheter according to claim 18,
wherein the anti-twist feature interlocks the flexible videoscope to the distal tip of the catheter body and thereby provides anti-rotational stability to the camera.

20. The steerable catheter according to claim 18,
wherein a cross sectional area of the housing portion and an overall volume of the anti-twist feature is minimized to optimize fluid flow through the tool channel by guiding fluids around the camera of the flexible videoscope.

21. The steerable catheter according to claim 1,
wherein the positioning mechanism includes a housing portion attachable to the imaging device and the anti-twist feature includes one or more keying tabs having curved surfaces configured to be pressure fit into against the inner diameter of the tool channel at the distal tip of the catheter body.

22. The steerable catheter according to claim 1,
wherein the positioning mechanism includes a housing portion attachable to the imaging device and the anti-twist feature includes one or more keying tabs having straight linear edges configured to be pressure fit against the inner diameter of the tool channel at the distal tip of the catheter body.

23. The steerable catheter according to claim 1,
wherein the positioning mechanism includes a housing portion made of circular or semi-circular rings of metallic wire attachable to the imaging device, and the anti-twist feature includes one or more keying tabs made of portions of metallic wire protruding outward from the housing portion and spanning in a lengthwise direction to connect the circular or semi-circular rings of metallic wire, and
wherein the portions of metallic wire protruding outward from the housing portion and connecting the circular or semi-circular rings of metallic wire are configured to be pressure fit against the inner diameter of the tool channel at the distal tip of the catheter body.

24. The steerable catheter according to claim 1,
wherein, when the housing portion attached to the imaging device is inserted into the tool channel, the one or more bumps are configured to prevent the imaging device from protruding beyond the distal end of the catheter body.

25. The steerable catheter according to claim 1,
wherein the elliptical tube is configured to house the imaging device inside the elliptical tube in a predetermined orientation, and the elliptical tube includes one or more recesses that are configured to fit into at least one of the one or more bumps of the tool channel.

26. The steerable catheter according to claim 25,
wherein, at the distal end of the catheter body, the tool channel includes a cylindrical surface that extends through the distal portion in a lengthwise direction, and the one or more bumps function as linear keying tabs facing radially inward formed in the lengthwise direction on the cylindrical surface of the tool channel,
wherein the one or more recesses function as linear keyways facing radially outward from the elliptical tube and extending in the lengthwise direction of the tool channel, and
wherein, when the positioning mechanism coupled to the imaging device is inserted into the tool channel, at least one of the linear keying tabs fits into one of the linear keyways thereby interlocking the imaging device to the catheter body.

* * * * *